(12) United States Patent
Alessandrini et al.

(10) Patent No.: US 6,319,955 B1
(45) Date of Patent: *Nov. 20, 2001

(54) USE OF MEK1 INHIBITORS AS PROTECTIVE AGENTS AGAINST DAMAGE DUE TO ISCHEMIA

(75) Inventors: Alessandro Alessandrini, Cambridge; Joseph Bonventre, Wayland; Michael A. Moskowitz, Belmont, all of MA (US); Shobu Namura, Osaka (JP)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/684,040

(22) Filed: Oct. 6, 2000

Related U.S. Application Data

(63) Continuation-in-part of application No. 09/226,080, filed on Jan. 6, 1999, now Pat. No. 6,150,401.
(60) Provisional application No. 60/070,530, filed on Jan. 6, 1998.

(51) Int. Cl.[7] .................................................... A61K 31/13
(52) U.S. Cl. .............................................. 514/665
(58) Field of Search ............................................ 514/665

(56) References Cited

U.S. PATENT DOCUMENTS

| 5,459,144 | 10/1995 | Girijavallabhan et al. . |
| 5,525,625 | 6/1996 | Bridges et al. . |
| 5,633,237 | 5/1997 | Hansen, Jr. et al. . |
| 5,717,100 | 2/1998 | Selnick et al. . |
| 5,849,733 | 12/1998 | Kim . |
| 6,150,401 | * 11/2000 | Alessandrini et al. ................ 514/456 |

OTHER PUBLICATIONS

Bederson et al., *Stroke* 17:1304–1308, 1986.
Uemura et al., *Brain Res.* 542:343–347, 1991.
Hu et al., *J. Neurochemistry* 62:1357–1367, 1994.
Huang et al., *Science* 265:1883–1885, 1994.
Seko et al., *Circ. Res.* 78:82–90, 1996.
Aikawa et al., *J. Biol. Chem.* 100:1813–1821, 1997.
Muller et al., *J. Biol. Chem.* 272:23435–23439, 1997.
Kindy, *J. Cer. Blood Flow and Metab.* 13:372–377, 1993.
Namura et al., *Stroke* 29:326(P142), 1998.
Mizukami et al., *Biochem. J.* 323:785–790, 1997.
Dufourney et al., *J. of Biol. Chem.* 272(49):31163–31171, 1997.

* cited by examiner

Primary Examiner—Raymond Henley, III
(74) Attorney, Agent, or Firm—Wolf, Greenfield & Sacks P.C.

(57) ABSTRACT

The invention relates to the use of MEK1 inhibitors to reduce tissue damage resulting from ischemia and/or reperfusion, particularly brain damage associated with ischemia resulting from stroke. Pharmaceutical compositions, kits and perfusion fluids including MEK1 inhibitors are also provided.

14 Claims, 12 Drawing Sheets

REDUCTION IN ERK1/2 PHOSPHORYLATION
IN THE PRESENCE OF PD98059
DMSO 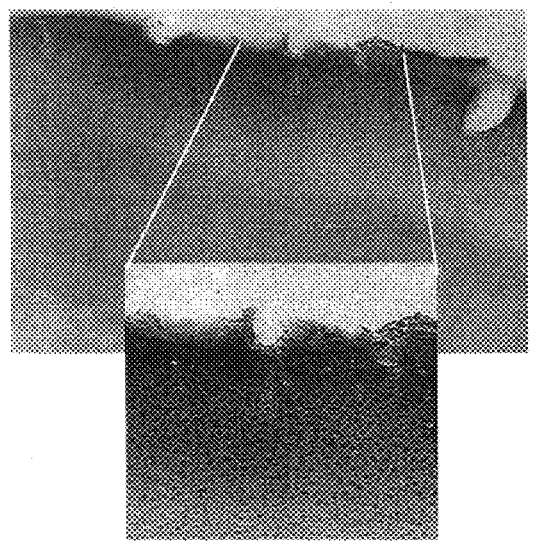 PD98059 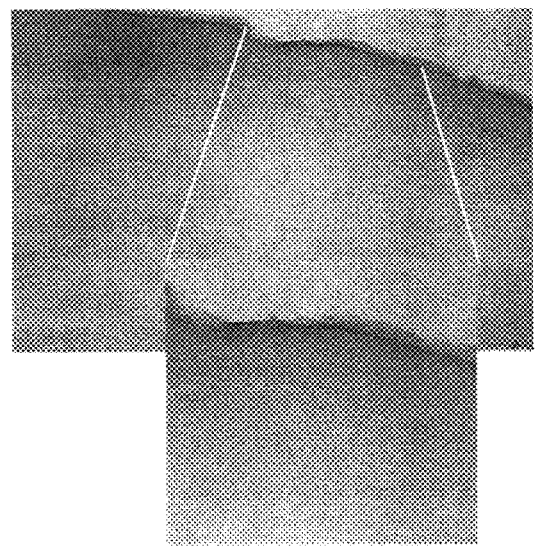
Fig. 3

EFFECT OF PD98059 ON INFARCT VOLUME 72 HR AFTER 2 HR ISCHEMIA

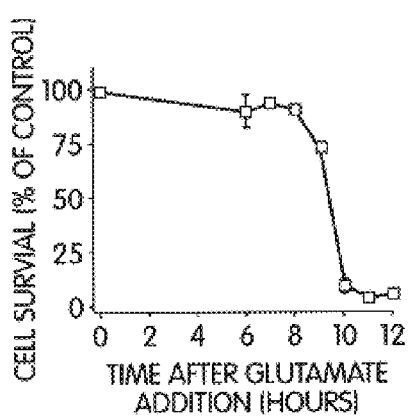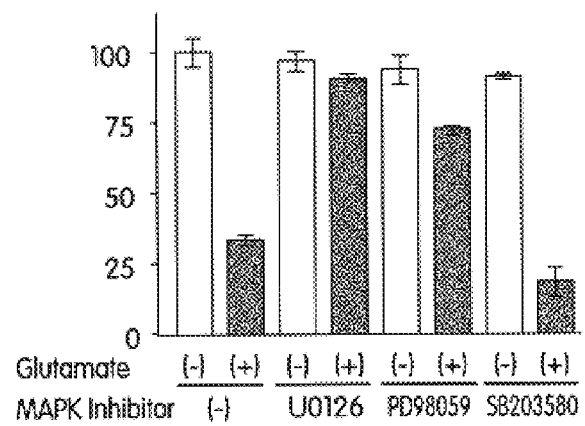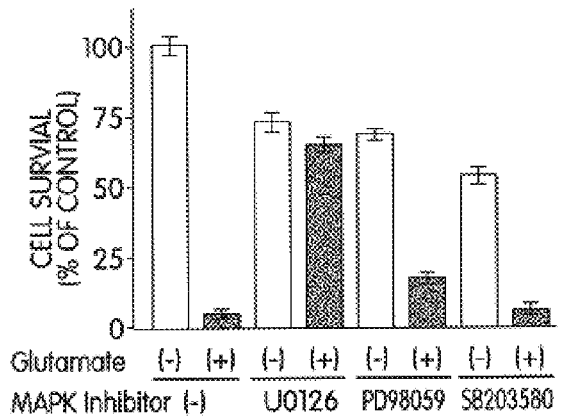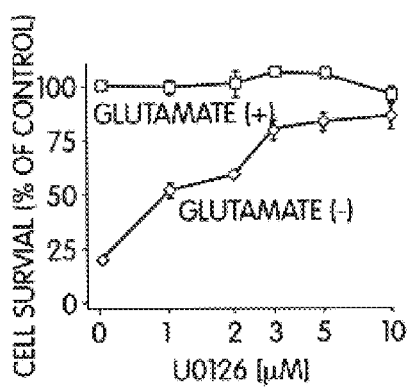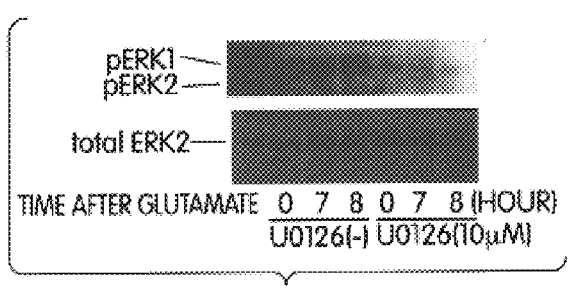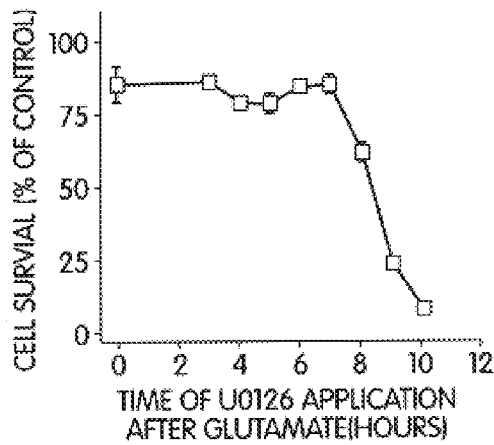

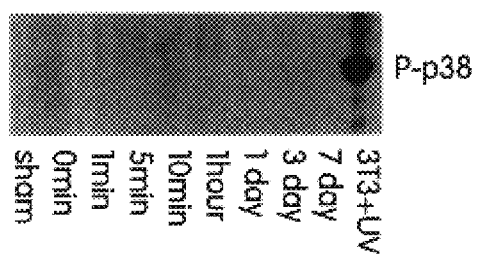
Fig. 10A
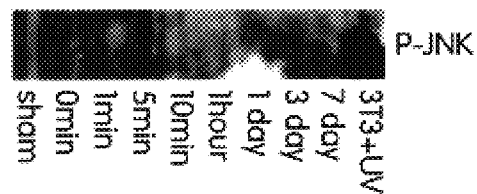
Fig. 10B
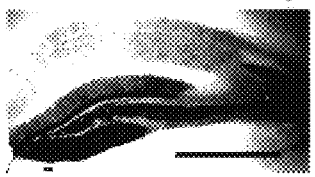
Fig. 11A
Fig. 11B

USE OF MEK1 INHIBITORS AS PROTECTIVE AGENTS AGAINST DAMAGE DUE TO ISCHEMIA

RELATED APPLICATIONS

This application is a continuation-in-part of U.S. Ser. No. 09/226,080, filed Jan. 6, 1999 and now issued as U.S. Pat. No. 6,150,401, which claims priority under 35 U.S.C. §119 from U.S. provisional application Ser. No. 60/070,530, filed Jan. 6, 1998.

GOVERNMENT SUPPORT

This work was funded in part by the National Institutes of Health under grant number 5P50NS10828-21. The government may retain certain rights in this invention.

FIELD OF THE INVENTION

The invention relates to treatments for tissue damage associated with ischemia, particularly brain damage associated with ischemia resulting from stroke.

BACKGROUND OF THE INVENTION

Ischemic diseases are significant causes of mortality in industrialized nations. It is well established that tissue damage results from ischemia (stoppage of blood flow to the tissue) followed by reperfusion of the tissue. The ischemic injury with the consecutive reperfusion is responsible for the disturbance of microcirculation with ensuing tissue damage and organ dysfunction.

One well-known example of ischemia and its effects is stroke, which is a condition resulting from a reduction or blockage of blood flow to the brain (cerebral ischemia). About 500,000 Americans suffer strokes each year, 80% of which are caused by a blood clot blocking one of the cerebral blood vessels. Symptoms of stroke include weakness, numbness or paralysis of the face, arm or leg; sudden loss or dimness of vision; loss of speech or difficulty using or understanding language; sudden, severe unexplained headache; or unexplained dizziness, unsteadiness or sudden falls (particularly if associated with one of the above symptoms).

Other organs are also affected by ischemia. For example, tissues such as kidney, heart, liver, pancreas, lung, intestine, are also known to sustain damage following ischemia and reperfusion.

The phosphorylation of ERK/MAP kinase in response to brain ischemia has been demonstrated previously. However, it is not known what, if any, role the ERK/MAP kinase pathway plays in the causation of tissue damage following ischemia and/or reperfusion.

SUMMARY OF THE INVENTION

It has now been discovered that MEK1 kinase activity is involved in ischemia-induced tissue damage. Using a mouse model of stroke in which permanent or transient focal cerebral ischemia is induced by middle cerebral artery occlusion, it has been demonstrated that MEK1 inhibitors can decrease the tissue damage which results from ischemia and reperfusion, in some cases even if the MEK1 inhibitor is administered after the onset of ischemia. It also has been demonstrated that MEK1 inhibitors can protect cells from glutamate toxicity and hypoxia.

According to one aspect of the invention, a method for treating a subject having a condition characterized by ischemia is provided. The method includes administering to a subject in need of such treatment a MEK1 inhibitor in an amount effective to reduce MEK1 activity, wherein the subject is free of symptoms otherwise calling for treatment with the MEK1 inhibitor. In certain embodiments, the symptoms otherwise calling for treatment with the MEK1 inhibitor are the symptoms of a proliferative disease. In other embodiments, the MEK1 inhibitor is selected from the group consisting of small molecule organic compounds, inhibitory antibodies, synthetic kinase substrate peptides, dominant negative MEK1 proteins, .antisense nucleic acids, and ribozymes which reduce the expression of translatable MEK1 transcripts. Preferably the MEK1 inhibitor is a small molecule organic compound, particularly a tricyclic flavone or a (phenylthio)butadiene compounds. In certain preferred embodiments, the MEK1 inhibitor is 2-(2-amino-3-methoxyphenyl)-4-oxo-4H-[1]benzopyran (PD98059), 1,4-diamino-2,3-dicyano-1,4-bis-(phenylthio)butadiene (U0125) or 1,4-diamino-2,3-dicyano- 1,4-bis-(2-aminophenylthio)butadiene (U0126). In particularly preferred embodiments the MEK1 inhibitor is (1,4-diamino-2, 3-dicyano-1,4-bis-(2-aminophenylthio)butadiene (U0126). In other preferred embodiments, the MEK1 inhibitor is administered to a subject who has had an ischemic stroke, or is administered prophylactically to a subject at risk of having an ischemic stroke. It is preferred that the MEK1 inhibitor is administered parenterally, particularly intravenously.

According to another aspect of the invention, a pharmaceutical composition is provided. The pharmaceutical composition includes a MEK1 inhibitor and a non-MEK1 inhibitor anti-stroke agent, together in an amount effective for treating an ischemic condition. Preferred inhibitors and agents are as described elsewhere.

According to still another aspect of the invention, a kit is provided. The kit includes a package housing a first container containing a MEK1 inhibitor, and instructions for using the MEK1 inhibitor in the treatment of an ischemic condition. In certain embodiments, the kit also includes a second container containing a non-MEK1 inhibitor anti-strokf agent.

According to another aspect of the invention, a medical product is provided which includes an isolated organ in a perfusion fluid containing a MEK1 inhibitor.

According to another aspect of the invention, a medical product is provided which includes an organ perfusion fluid containing a MEK1 inhibitor.

In another aspect of the invention, the use of the foregoing MEK1 inhibitors in the preparation of a medicament for the foregoing treatments of conditions characterized by ischemia, particularly stroke, is provided.

These and other objects of the invention will be described in further detail in connection with the detailed description of the invention.

BRIEF DESCRIPTION OF THE FIGURES

FIG. 3 shows the immunohistochemistry of phosphorylated ERK1/2 in brain slices of animals treated with PD98059 or DMSO control following ischemia and reperfusion.

FIG. 5 shows that MEK inhibition blocks cell death induced by glutamate toxicity. (A) Extracellular glutamate (5 mM) induces death in HT22 cells by incubation for 10 hours. Cell viability was determined by the MTT assay; percent cell survival is presented as mean±SEM (n=4). (B,C) Effects of U0126 (Promega), PD98059 (New England Biolabs) and SB203580 (Tocris) on injury in HT22 cells by incubating with glutamate (5 mM) for 9 hr (B) or 24 hr (C) was assessed by MTT assay 24 hr after addition of glutamate. Percent cell survival is presented as mean±SEM (n=4). Pretreatment with SB203580 (50 $\mu$M), an inhibitor of p38 MAP kinase and SAPKs/JNKs at this concentration, does not protect HT22 cells. PD98059 (50 $\mu$M) and U0126 (10 $\mu$M) MEK1-specific inhibitors attenuated cell injury (B, C). (D) Dose-dependent protection with U0126 in HT22 cells treated with glutamate (5 mM) for 24 hours (filled diamonds). U0126 is not toxic up to 10 $\mu$M (open squares). (E) U0126 inhibits the phosphorylation of ERK1/2 in HT22 cells treated with glutamate, however does not affect total ERK1/2 protein levels. Immunoblotting was done with an antibody that specifically recognizes phosphorylated ERK1 and ERK2 (upper panel; New England Biolabs, dilution 1:1000) or with an antibody that recognizes ERK1/2 regardless of its phosphorylation state (lower panel; New England Biolabs, dilution 1:1000). (F) Effect of delayed application of U0126 on cell survival after glutamate toxicity. Ten $\mu$M U0126 was added to HT22 cells at the indicated time after exposure to 5 mM glutamate, and cell survival was determined by MTT assay 24 hours after glutamate addition. Percent cell survival is presented as mean±SEM (n=4). Application of U0126 was initiated up to 7 hours after glutamate completely inhibited cell death.

FIG. 10 Time-dependent changes in phospho-p38 mitogen-activated protein kinase (A) and phospho-c-Jun N-terminal kinase (JNK) (B) in the hippocampus after 3.5 min bilateral carotid artery occlusion (BCAO). Ultraviolet-treated NIH3T3 cell lysate (3T3+UV) was used as a control for p38 and JNK phosphorylation. Neither phosphorylation of p38 protein kinase nor phosphorylation of JNK was observed in the hippocampus over the reperfusion periods.

FIG. 11 Phospho-ERK1/2 immunostaining using brain sections through the hippocampus after 10 min reperfusion following bilateral carotid artery occlusion (BCAO). (A) The gerbil was subjected to 1 min BCAO, which does not induce cell death in the hippocampus. Increased phospho-ERK1/2 immunostaining is observed in the dentate gyrus and mossy fibers; however, phospho-ERK1/2 immunostaining is barely detectable in the CA1 pyramidal cell layer. Scale bar: 1 mm. (B) The gerbils were treated with ischemic preconditioning (Isc. Precon.), lesioning of the ipsilateral entorhinal cortex (Ent. Lesion.), or hyperthermia (32° C.), and then subjected to 3.5 min BCAO. The brains were examined at 10 min after reperfusion. Phospho-ERK1/2 immunostaining is barely detectable in the CA1 pyramidal cell layer. Scale bar: 1 mm.

DETAILED DESCRIPTION OF THE INVENTION

Figure 1:
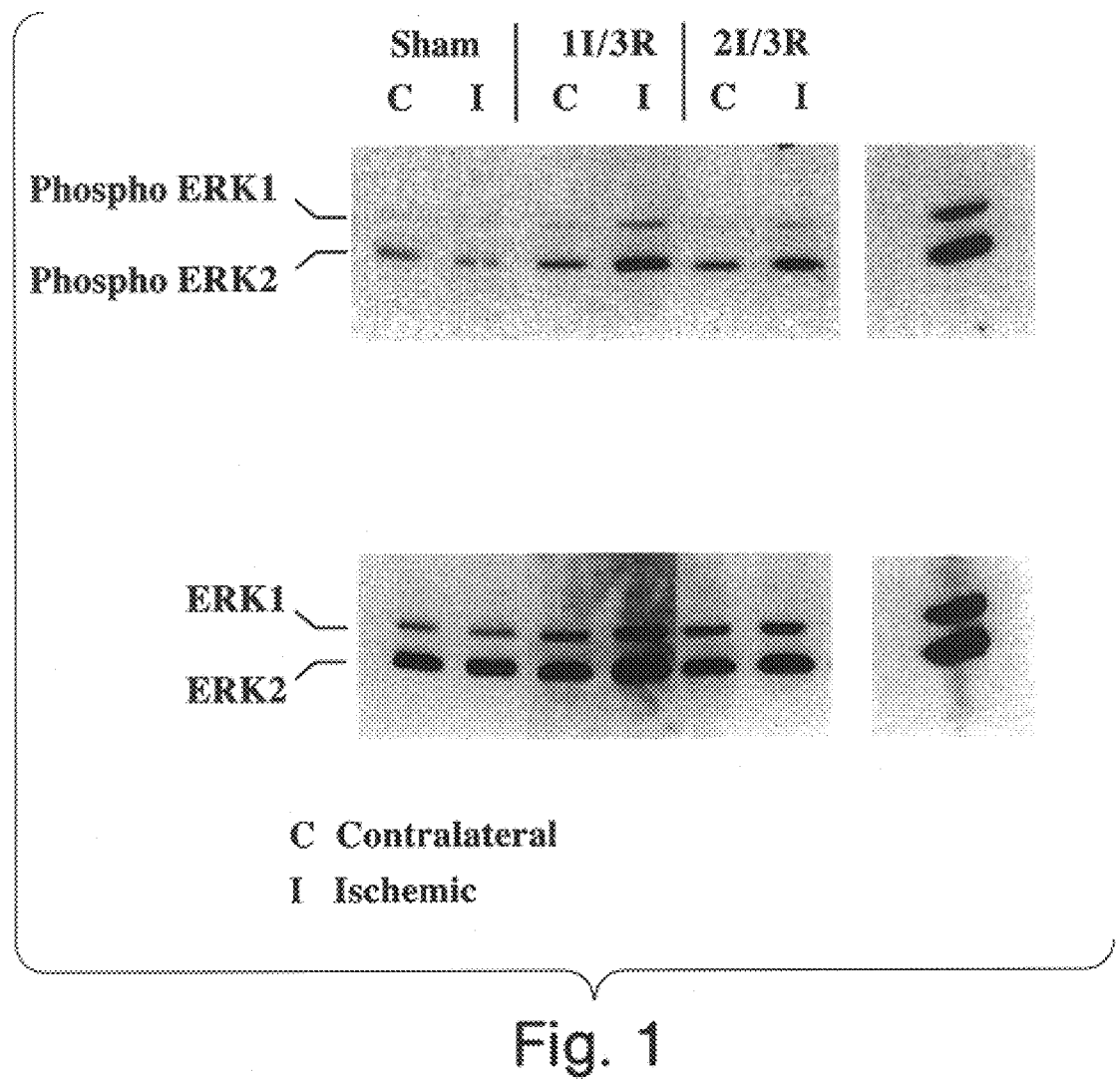
FIG. 1 depicts a Western blot which shows the phosphorylation of ERK1 and ERK2 following cerebral ischemia and reperfusion.

Ischemia is a condition characterized by a stoppage of blood flow to a tissue or organ. The stoppage may result from a blockage in the blood vessel supplying the tissue or organ (e.g. a stroke), or may result when the heart stops beating (e.g. a heart attack). Reperfusion is the term which describes the restarting of the supply of blood to the organ or tissue following ischemia.

The present invention utilizes the unexpected finding that classes of compounds (MEK1 inhibitors) can relieve damage due to ischemia by inhibiting the MEK1 kinase. MEK1 is a dual specificity kinase that activates the MAP kinases ERK1 and ERK2 by phosphorylation on threonine and tyrosine. A MEK1 inhibitor, as used herein, is a compound which inhibits MEK1 kinase activity. By inhibition of MEK1 activity is meant the partial or complete inhibition of the MEK1 kinase activity in the affected tissue. This may be a reduction in the kinase activity of MEK1 to a level below that found under normal physiological conditions (which may vary from subject to subject if used prophylactically or below that found under the conditions prevailing in the ischemic tissue if used acutely.

Compounds which are useful as MEK1 inhibitors include compounds which act on the MEK1 protein to directly inhibit MEK1 activity and compounds which indirectly inhibit MEK1 activity by reducing MEK1 expression at the stages of transcription and/or translation of the MEK1 gene. Inhibitors of MEK1 activity include compounds which bind to MEK1 and inhibit the enzymatic activity, including small molecule organic compounds, inhibitory antibodies, synthetic kinase substrate peptides and the like. Inhibitors of MEK1 activity also include variants of MEK1 having reduced activity, e.g. dominant negative MEK1 proteins having an inactivated kinase. Compounds which reduce MEK1 expression include antisense nucleic acids and ribozymes which reduce the expression of translatable MEK1 transcripts.

Preferred MEK1 inhibitors include flavone compounds and a particularly preferred flavone is the flavone compound 2-(2-amino-3-methoxyphenyl)-4-oxo-4H-[1]benzopyran (also known as 2'-amino-3'-methoxyflavone) described in U.S. Pat. No. 5,525,625. The formula of the compound is:

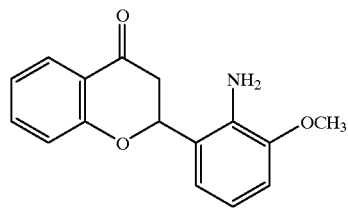

Variants of the foregoing flavone compound which retain the MEK1 inhibitory activity of the foregoing flavone compound also can be used in accordance with the invention. For example, different alkyl groups can be substituted for the methyl group at the 3 position of the phenyl ring. As one example, an ethyl group can be substituted for the methyl group to prepare the 3-ethoxy flavone derivative. Other examples of alkyl substitutions will be known to one of ordinary skill in the art and are not detailed further here. Still other types of chemical modifications can be made to the foregoing flavone to prepare compounds useful in the methods detailed herein, and such compounds tested for MEK1 inhibitory activity as detailed herein and in U.S. Pat. No. 5,525,625, with no more than routine experimentation.

Other preferred MEK1 inhibitors include (phenylthio) butadiene compounds; particularly preferred are the compounds (1,4-diamino-2,3-dicyano-1,4-bis-(2-phenylthio) butadiene (U0125) and (1,4-diamino-2,3-dicyano-1,4-bis-(2-aminophenylthio)butadiene (U0126) described by Favata et al. (*J. Biol. Chem.* 273:18623–18632, 1998). The formulas of the compounds are:

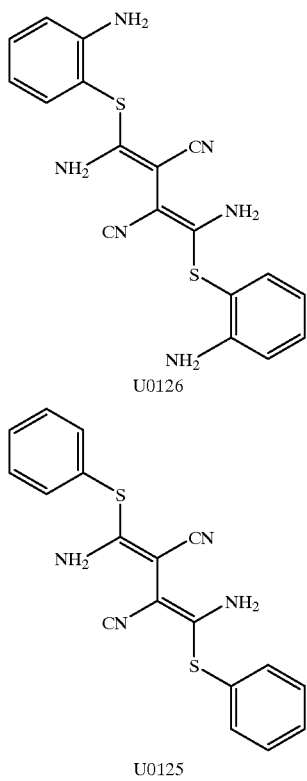

U0126

U0125

Variants of the foregoing (phenylthio)butadiene compounds which retain the MEK1 inhibitory activity of the (phenylthio)butadiene compounds also can be used in accordance with the invention. Substitutions preferably are made for the phenyl rings, or for one or both of the NH$_2$ group on the phenyl rings of U0126, above. Chemical groups which can be added to one or both ends of the molecule include: hydrido, alkyl, alkenyl, alkynyl, cycloalkyl, heterocycyl, aryl, heteroaryl, alkoxy, aryloxy, sulfoxy, acyl, amino, acyloxy, acylamino, carboalkoxy, carboxyamido, carboxyamido, halo and thio groups. Substitutions also can be made for the terminal groups on the butadiene portion of the molecule (i.e., CN, NH$_2$)

Molecular terms, when used in this application, have their common meaning unless otherwise specified. The term "hydrido" denotes a single hydrogen atom (H). The term "acyl" is defined as a carbonyl radical attached to an alkyl, alkenyl, alkynyl, cycloalkyl, heterocycyl, aryl or heteroaryl group, examples of such radicals being acetyl and benzoyl. The term "amino" denotes a nitrogen radical containing two substituents independently selected from the group consisting of hydrido, alkyl, cycloalkyl, heterocyclyl, aryl, and heteroaryl. The term "acyloxy" denotes an oxygen radical adjacent to an acyl group. The term "acylamino" denotes a nitrogen radical adjacent to an acyl group. The term "carboalkoxy" is defined as a carbonyl radical adjacent to an alkoxy or aryloxy group. The term "carboxyamido" denotes a carbonyl radical adjacent to an amino group. The term "carboxy" embraces a carbonyl radical adjacent to an alkyl, alkenyl, alkynyl, cycloalkyl, heterocyclyl, aryl or heteroaryl group. The term "halo" is defined as a bromo, chloro, fluoro or iodo radical. The term "thio" denotes a radical containing a substituent group independently selected from hydrido, alkyl, cycloalkyl, heterocyclyl, aryl and heteroaryl, attached to a divalent sulfur atom, such as, methylthio and phenylthio.

The term "alkyl" is defined as a linear or branched, saturated radical having one to about ten carbon atoms unless otherwise specified. Preferred alkyl radicals are "lower alkyl" radicals having one to about five carbon atoms. One or more hydrogen atoms can also be replaced by a substitutent group selected from acyl, amino, acylamino, acyloxy, carboalkoxy, carboxy, carboxyamido, cyano, halo, hydroxy, nitro, thio, alkyl, alkenyl, alkynyl, cycloalkyl, heterocyclyl, aryl, heteroaryl, alkoxy, aryloxy, sulfoxy, and formyl. Examples of alkyl groups include methyl, tert-butyl, isopropyl, and methoxymethyl. The term "alkenyl" embraces linear or branched radicals having two to about twenty carbon atoms, preferably three to about ten carbon atoms, and containing at least one carbon-carbon double bond. One or more hydrogen atoms can also be replaced by a substituent group selected from acyl, amino, acylamino, acyloxy, carboalkoxy, carboxy, carboxyamido, cyano, halo, hydroxy, nitro, thio, alkyl, alkenyl, alkynyl, cycloalkyl, heterocyclyl, aryl, heteroaryl, alkoxy, aryloxy, sulfoxy, and formyl. Examples of alkenyl groups include ethylenyl or phenyl ethylenyl. The term "alkynyl" denotes linear or branched radicals having from two to about ten carbon atoms, and containing at least one carbon-carbon triple bond. One or more hydrogen atoms can also be replaced by a substituent group selected from acyl, amino, acylamino, acyloxy, carboalkoxy, carboxy, carboxyamido, cyano, halo, hydroxy, nitro, thio, alkyl, alkenyl, alkynyl, cycloalkyl, heterocyclyl, aryl, heteroaryl, alkoxy, aryloxy, sulfoxy, and formyl. Examples of alkynyl groups include propynyl. The term "aryl" denotes aromatic radicals in a single or fused carbocyclic ring system, having from five to twelve ring members. One or more hydrogen atoms may also be replaced by a substituent group selected from acyl, amino, acylamino, acyloxy, carboalkoxy, carboxy, carboxyamido, cyano, halo, hydroxy, nitro, thio, alkyl, alkenyl, alkynyl, cycloalkyl, heterocyclyl, aryl, heteroaryl, alkoxy, aryloxy, sulfoxy, and formyl. Examples of aryl groups include phenyl, naphthyl, biphenyl, terphenyl. "Heteroaryl" embraces aromatic radicals which contain one to four hetero atoms selected from oxygen, nitrogen and sulfur in a single or fused heterocyclic ring system, having from five to fifteen ring members. One or more hydrogen atoms may also be replaced by a substituent group selected from acyl, amino, acylamino, acyloxy, carboalkoxy, carboxy, carboxyamido, cyano, halo, hydroxy, nitro, thio, alkyl, alkenyl, alkynyl, cycloalkyl, heterocyclyl, aryl, heteroaryl, alkoxy, aryloxy, sulfoxy, and formyl. Examples of heteroaryl groups include, pyridinyl, thiazolyl, thiadiazoyl, isoquinolinyl, pyrazolyl, oxazolyl, oxadiazoyl, triazolyl, and pyrrolyl groups.

The term "cycloalkyl" is defined as a saturated or partially unsaturated carbocyclic ring in a single or fused carbocyclic ring system having from three to twelve ring members. One or more hydrogen atoms may also be replaced by a substituent group selected from acyl, amino, acylamino, acyloxy, carboalkoxy, carboxy, carboxyamido, cyano, halo, hydroxy, nitro, thio, alkyl, alkenyl, alkynyl, cycloalkyl, heterocyclyl, aryl, heteroaryl, alkoxy, aryloxy, sulfoxy, and formyl. Examples of a cycloalkyl group include cyclopropyl, cyclobutyl, cyclohexyl, and cycloheptyl. The term "heterocyclyl" embraces a saturated or partially unsaturated ring containing zero to four hetero atoms selected from oxygen, nitrogen and sulfur in a single or fused heterocyclic ring system having from three to twelve ring members. One or more hydrogen atoms may also be replaced by a substituent group selected from acyl, amino, acylamino, acyloxy, carboalkoxy, carboxy, carboxyamido, cyano, halo, hydroxy, nitro, thio, alkyl, alkenyl, alkynyl, cycloalkyl, heterocyclyl, aryl, heteroaryl, alkoxy, aryloxy, sulfoxy, and formyl. Examples of a heterocyclyl group include morpholinyl, piperidinyl, and pyrrolidinyl. The term "alkoxy" denotes oxy-containing radicals substituted with an alkyl, cycloalkyl or heterocyclyl group. Examples include methoxy, tert-butoxy, benzyloxy and cyclohexyloxy. The term "aryloxy" denotes oxy-containing radicals substituted with an aryl or heteroaryl group. Examples include phenoxy. The term "sulfoxy" is defined as a hexavalent sulfur radical bound to two or three substituents selected from the group consisting of oxo, alkyl, cycloalkyl, heterocyclyl, aryl and heteroaryl, wherein at least one of said substituents is oxo.

As mentioned above, the invention embraces the use of antisense oligonucleotides that selectively bind to a nucleic acid molecule encoding a MEK1 polypeptide, to decrease MEK1 transcription or translation. Antisense molecules, in this manner, can be used to decrease or prevent the effects of ischemia mediated by MEK 1.

As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript.

Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions. Based upon the MEK1 cDNA sequence (GenBank accession numbers L02526 (mouse) and L11284 (human)), or upon allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least 10 and, more preferably, at least 15 consecutive bases which are complementary to the target, although in certain cases modified oligonucleotides as short as 7 bases in length have been used successfully as antisense oligonucleotides (Wagner et al., *Nature Biotechnol.* 14:840–844, 1996). Most preferably, the antisense oligonucleotides comprise a complementary sequence of 20–30 bases.

Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., *Cell Mol. Neurobiol.* 14(5):439–457, 1994) and at which proteins are not expected to bind. Finally, one of ordinary skill in the art may easily derive the genomic DNAs corresponding to the MEK1 cDNAs and thus the present invention also provides for the use of antisense oligonucleotides which are complementary to MEK1 genomic DNAs. Similarly, the use of antisense to MEK1 cDNAs and genomic DNAs of other species are enabled without undue experimentation.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleotide linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose. Modified oligonucleotides also can include base analogs such as C-5 propyne modified bases (Wagner et al., *Nature Biotechnology* 14:840–844, 1996). The present invention, thus, contemplates the use of pharmaceutical preparations containing modified antisense molecules that are complementary to and hybridizable with, under physiological conditions, nucleic acids encoding MEK1 polypeptides, together with pharmaceutically acceptable carriers.

The invention also provides, in certain embodiments, the use of "dominant negative" MEK1 polypeptides. A dominant negative polypeptide is an inactive variant of a protein, which, by interacting with the cellular machinery, displaces an active protein from its interaction with the cellular machinery or competes with the active protein, thereby reducing the effect of the active protein. For example, dominant negative MEK 1 proteins include MEK1 proteins having a catalytically-inactive kinase domain which interacts normally with target proteins but does not phosphorylate the target proteins, or which does not interact with normally with target proteins, or both. Dominant negative MEK1 proteins include variants in which a portion of the kinase domain has been mutated or deleted to reduce or eliminate substrate binding or kinase activity.

The end result of the expression of a dominant negative MEK1 polypeptide in a cell is a reduction in function of active proteins. One of ordinary skill in the art can assess the potential for a dominant negative variant of a protein, and using standard mutagenesis techniques to create one or more dominant negative variant polypeptides. For example, given the nucleotide sequence of MEK1, one of ordinary skill in the art can modify the sequence of the MEK1 polypeptide by site-specific mutagenesis, scanning mutagenesis, partial gene deletion or truncation, and the like. See, e.g., U.S. Pat. No. 5,580,723 and Sambrook et al., *Molecular Cloning. A Laboratory Manual,* Second Edition, Cold Spring Harbor Laboratory Press, 1989. The skilled artisan then can test the population of mutagenized polypeptides for diminution in a selected activity (e.g., MEK1 kinase activity). Other similar methods for creating and testing dominant negative variants of a protein will be apparent to one of ordinary skill in the art.

The invention also embraces MEK1 binding agents which can be antibodies or fragments of antibodies having the ability to selectively bind to MEK1 polypeptides. Such agents can be used to inhibit the native activity of the MEK1 polypeptides by binding to such polypeptides. Antibodies include polyclonal and monoclonal antibodies, prepared according to conventional methodology.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology,* 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. See, e.g., U.S. Pat. Nos. 4,816,567, 5,225,539, 5,585,089, 5,693,762 and 5,859,205.

Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

Thus, the invention involves polypeptides of numerous size and type that bind specifically to MEK1 polypeptides, and complexes of both MEK1 polypeptides and their binding partners. These polypeptides may be derived also from sources other than antibody technology. For example, such polypeptide binding agents can be provided by degenerate peptide libraries which can be readily prepared in solution, in immobilized form or as phage display libraries. Combinatorial libraries also can be synthesized of peptides containing one or more amino acids. Libraries further can be synthesized of peptoids and non-peptide synthetic moieties.

Phage display can be particularly effective in identifying binding peptides useful according to the invention, including human antibodies. Briefly, one prepares a phage library (using e.g. m13, fd, or lambda phage), displaying inserts from 4 to about 80 amino acid residues using conventional procedures. The inserts may represent, for example, a completely degenerate or biased array. One then can select phage-bearing inserts which bind to the MEK1 polypeptide. This process can be repeated through several cycles of reselection of phage that bind to the MEK1 polypeptide. Repeated rounds lead to enrichment of phage bearing particular sequences. DNA sequence analysis can be conducted to identify the sequences of the expressed polypeptides. The minimal linear portion of the sequence that binds to the MEK1 polypeptide can be determined. One can repeat the procedure using a biased library containing inserts containing part or all of the minimal linear portion plus one or more additional degenerate residues upstream or downstream thereof. Yeast two-hybrid screening methods also may be used to identify polypeptides that bind to the MEK1 polypeptides. Thus MEK1 polypeptides, or fragments thereof, can be used to screen peptide libraries, including phage display libraries, to identify and select peptide binding partners of MEK1. Additional methodologies are described by Zhang et al., *Nature Biotechnol.* 18:71–74, 2000. Such molecules can be used, as described, for interfering directly with the functioning of MEK1 polypeptides and for other purposes that will be apparent to those of ordinary skill in the art.

Several tests can be used to identify compounds which are specific inhibitors of MEK1 activity. For example U.S. Pat. No. 5,525,625, the disclosure of which is incorporated herein by reference, describes several assays which are useful for determining the MEK1 inhibitory potential of a test compound. The assays include in vitro kinase assays, whole cell kinase assays, and cell growth assays including assays of monolayer growth and growth in soft agar. The Examples below provide an in vivo assay of focal cerebral ischemia and in vitro cell-based assays for testing the activity of MEK1 inhibitors. Additional assays are described by Favata et al. (J. Biol. Chem. 273:18623–18632, 1998), the disclosure of which is incorporated by reference. If the test compound is able to inhibit the MEK 1 activity, then it is a compound which is useful in the treatment of ischemia, particularly stroke, and other conditions including hypoxia and glutamate toxicity. The test compound can be determined readily to be a specific inhibitor of MEK1 activity.

The present invention is useful whenever it is desirable to prevent, inhibit altogether or reduce damage due to ischemia. The invention thus is useful in the treatment of ischemia, particularly in the prophylactic treatment of ischemia. In particular, the methods of treatment disclosed herein can be used to reduce brain injury resulting from strokes and/or perioperative ischemia during neural surgery. The methods of treatment disclosed herein can be used to reduce tissue injury resulting from ischemia in other organs including heart, kidney, pancreas, lung, intestine and the like.

The invention is also useful for the treatment of hypoxia. Hypoxia, as used herein, refers to a lack of oxygen in tissues, particularly the brain. Hypoxia is characterized by gait and speech disturbances, tremors and weakness. The brain may suffer from hypoxia even if blood flow and blood pressure are normal, although hypoxia also may accompany interrupted blood flow or low blood pressure. Causes of hypoxia include chronic pulmonary disease, pulmonary emboli, alveolar hypotension, anemia and carbon monoxide poisoning.

The invention further is useful for the treatment of glutamate toxicity. Glutamate toxicity (or excitotoxicity) is the overstimulation of neurons by excessive amounts of the neurotransmitter glutamate, which can lead to neuronal cell damage or cell death.

The invention is particularly directed to a patient population never before treated with drugs useful according to the methods of the invention, including patients who are not suffering from a proliferative disorder such as cancer, psoriasis or restenosis. In other words, the treatment preferably is directed to patient populations that otherwise are free of symptoms that call for treatment with any of the drugs useful according to the invention.

When administered, the formulations of the invention are applied in pharmaceutically acceptable amounts and in pharmaceutically acceptable compositions. Such preparations may routinely contain salts, buffering agents, preservatives, compatible carriers, and optionally other therapeutic ingredients. Such pharmacologically and pharmaceutically acceptable salts include, but are not limited to, those prepared from the following acids: hydrochloric, hydrobromic, sulphuric, nitric, phosphoric, maleic, acetic, salicylic, p-toluene sulfonic, tartaric, citric, methane sulfonic, formic, malonic, succinic, naphthalene-2-sulfonic, and benzene sulfonic. Also, pharmaceutically acceptable salts can be prepared as alkaline metal or alkaline earth salts, such as sodium, potassium or calcium salts of the carboxylic acid group.

The compounds useful in the invention may be delivered in a mixture with other anti-ischemia agents (particularly anti-stroke agents) which are non-MEK1 inhibitors. A non-MEK1 inhibitor anti-stroke agent is an anti-stroke agent which is not a MEK1 inhibitor as defined herein. One of ordinary skill in the art is familiar with a variety of non-MEK1 inhibitor anti-stroke agents which are used in the medical arts to treat ischemia such as stroke (e.g., thrombotic, embolic and/or hemorrhagic stroke). Such agents include antiplatelet agents, anticoagulation agents, thrombolytic agents including plasminogen activators, antithrombotics, neuroprotective agents, platelet activating factor antagonists, platelet aggregation inhibitors, post-stroke and post-head trauma treatments, cerebral ischemia agents, basic fibroblast growth factors and steroids Antiplatelet agents, which inhibit platelet aggregation, include aspirin, ticlopidine and dipyridamole.

Anticoagulation agents reduce or prevent the coagulation of blood components and thus reduce or prevent clot formation; common anticoagulation agents include coumarin and heparin.

Thrombolytic agents function by lysing the clot which causes the ischemia. Commonly used thrombolytic agents include urokinase, streptokinase and tissue plasminogen activator (alteplase, tPA). Various modified forms of tPA ("modified tPA") have been characterized and are known to those skilled in the art. Modified tPA includes, but is not limited to, variants having deleted or substituted amino acids or domains, variants conjugated to other molecules, and variants having modified glycosylation. For example, PCT Publication No. W093/24635 discloses tPA variants having an extra glycosylation site at any of the amino acid positions 103–105 and the native glycosylation site removed at position 117 of the native human tPA. The amino acid number refers to the amino acid in that position of the mature, wild-type tPA polypeptide as disclosed in U.S. Pat. No. 4,766,075. The disclosed variants may also include at least one amino acid substituted in the 296–299 position with alanine and/or a substitution of the amino acids at positions 274–277 of wild type tPA (phenylalanine, arginine, isoleucine, lysine) with leucine, histidine, serine, and threonine, respectively. Triple mutants of tPA also are disclosed, including the specific molecule: T103N, N117Q, KHRR (296–299) AAAA t-PA (TNK t-PA). EP 352,119 discloses vampire bat tPAs (Bat-PAs (H), (I), and (L)). Vampire bat-PAs are variants of native tPA having a variety of sequence modifications. Suzuki et al., (J. Cardiovasc. Pharmacal. 22:834–840, 1993) disclose tPA variants in which a cysteine at position 84 of the growth factor domain of native tPA is replaced by serine (C84S tPA). Although this variant retains the functional activity of native tPA, it has been shown to have a longer in vivo half life than native tPA.

Variants of tPA have been developed which retain tPA functionality but have reduced clearance rates. These variants include tPA molecules with deleted amino acids or domains, such as those described by Johannessen et al. (Throm. Haemostas. 63:54–59, 1990) and Sobel et al. (Circulation 81:1362–73, 1990); tPA molecules which have amino acid substitutions in the regions of 63–72 and 42–49, such as those described by Ahem et al. (J. Biol. Chem. 265:5540, 1990); and tPA molecules which have a glutamic acid substituted for the arginine at position 275 of the native t-PA molecule such as that described by Hotchkiss et al. (*Throm. Haemostas.* 55:491, 1987). tPA molecules conjugated to other molecules have also been found to have decreased clearance rates. For example, conjugation of tPA to polyethylene glycol has been shown to reduce the clearance rate of tPA, as disclosed in EP-A304,311. Conjugation of a tPA molecule to a monoclonal antibody has been shown to increase the half-life of tPA in vivo (EP A339,505).

Modification of glycosylation on native tPA has also been found to have an effect on clearance rates of tPA. PCT application WO89/11531 discloses several tPA variants having additional glycosylation sites, which also have decreased clearance rates. Other research has described tPA variants with reduced glycosylation, which also exhibit decreased clearance rates (Martin et al., *Fibrinolysis* 4:9, 1990). Each of the above references is hereby incorporated by reference.

Antithrombotics include anagrelide hydrochloride; bivalirudin; dalteparin sodium; danaparoid sodium; dazoxiben hydrochloride; efegatran sulfate; enoxaparin sodium; ifetroban; ifetroban sodium; tinzaparin sodium; and trifenagrel.

Neuroprotective agents include dizocilpine maleate.

Cardioprotectant agents including MPL-C, adenosine, and acadesine.

Platelet activating factor antagonists include lexipafant.

Platelet aggregation inhibitors include acadesine; beraprost; beraprost sodium; ciprostene calcium; itazigrel; lifarizine; oxagrelate.

Post-stroke and post-head trauma agents include citicoline sodium (cytidine 5'-diphosphocholine).

Cerebral ischemia agents include dextrorphan hydrochloride.

Additional anti-ischemia agents include N-methyl-D-aspartate (NMDA) receptor antagonists (preferably dizolcipine maleate (MK801); Simon et al., *Science* 226:850, 1984), certain immunosuppressants (preferably FK506 (tacrolimus); Sharkey et al., *Nature* 371:336, 1994; Butcher et al., *J. Neurosci.* 17:6939, 1997) or caspase inhibitors (preferably Z-Val-Ala-Asp-fluoromethylketone (zVAD-fmk); Hara et al., *Proc. Acad. Nat'l Sci. USA* 94:2007, 1997; Ma et al., *Br. J. Pharmacol.* 124:756, 1998).

The formulations of the invention are administered in effective amounts, alone or in a cocktail with one or more of the foregoing compounds. An effective amount is one sufficient to inhibit MEK1 activity, thereby effectively decreasing or preventing the deleterious effects of ischemia. Effective amounts will depend, of course, on the severity of the condition being treated; individual patient parameters including age, physical condition, size and weight; concurrent treatment; frequency of treatment; and the mode of administration. These factors are well known to those of ordinary skill in the art and can be addressed with no more than routine experimentation. It is preferred generally that a maximum dose be used, that is, the highest safe dose according to sound medical judgment.

Dosages are estimated based on the inhibition of MEK1 activity and the inhibition of the effects of ischemia in experimental models. Generally, daily oral prophylactic doses of active compounds will be from about 0.01 milligrams/kg per day to 2000 milligrams/kg per day. It is expected that oral doses in the range of 10 to 500 milligrams/kg, in one or several administrations per day, will yield the desired results. In the event that the response in a subject is insufficient at such doses, even higher doses (or effective higher doses by a different, more localized delivery route) may be employed to the extent that patient tolerance permits. Dose ranges can be adjusted as necessary for the treatment of ischemia in organs other than brain, i.e., other than for the treatment of stroke. Multiple doses per day are contemplated to achieve appropriate systemic levels of compounds.

A variety of administration routes are available. The particular mode selected will depend of course, upon the particular drug selected, the severity of the migraine state being treated and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, rectal, topical, nasal, transdermal or parenteral routes. The term "parenteral" includes subcutaneous, intravenous, intramuscular, or infusion. Intravenous and intramuscular routes are not particularly suited for long term therapy and prophylaxis. Intravenous administration is preferred in acute emergency situations. Oral administration will be preferred for prophylactic treatment because of the convenience to the patient as well as the dosing schedule.

The compositions may conveniently be presented in unit dosage form and may be prepared by any of the methods well known in the art of pharmacy. In general, the compositions are prepared by uniformly and intimately bringing the active compounds into association with a liquid carrier, a finely divided solid carrier, or both, and then, if necessary, shaping the product.

Compositions suitable for oral administration may be presented as discrete units such as capsules, cachettes, tablets, or lozenges, each containing a predetermined amount of the active compound. Other compositions include suspensions in aqueous liquors or non-aqueous liquids such as a syrup, an elixir, or an emulsion.

Other delivery systems can include time-release, delayed release or sustained release delivery systems. Such systems can avoid repeated administrations of the active compounds of the invention, increasing convenience to the subject and the physician. Many types of release delivery systems are available and known to those of ordinary skill in the art. They include polymer based systems such as polylactic and polyglycolic acid, polyanhydrides and polycaprolactone; nonpolymer systems that are lipids including sterols such as cholesterol, cholesterol esters and fatty acids or neutral fats such as mono-, di and triglycerides; hydrogel release systems; silastic systems; peptide based systems; wax coatings, compressed tablets using conventional binders and excipients, partially fused implants and the like. Specific examples include, but are not limited to: (a) erosional systems in which the polysaccharide is contained in a form within a matrix, found in U.S. Pat. No. 4,452,775 (Kent); U.S. Pat. No. 4,667,014 (Nestor et al.); and U.S. Pat. Nos. 4,748,034 and 5,239,660 (Leonard) and (b) diffusional systems in which an active component permeates at a controlled rate through a polymer, found in U.S. Pat. No. 3,832,253 (Higuchi et al.) and U.S. Pat. No. 3,854,480 (Zaffaroni). In addition, a pump-based hardware delivery system can be used, some of which are adapted for implantation.

Use of a long-term sustained release implant may be particularly suitable for prophylactic treatment of ischemia. "Long-term" release, as used herein, means that the implant is constructed and arranged to deliver therapeutic levels of the active ingredient for at least 30 days, and preferably 60 days. Long-term sustained release implants are well known to those of ordinary skill in the art and include some of the release systems described above.

The reduction of ischemic damage by MEK1 inhibitors also enables improvements in organ transplantation perfusion fluids used in the treatment, storage and transport of organs to be transplanted. Thus the invention also provides medical products useful in organ transplantation. In particular, the invention provides organ perfusion fluids containing a MEK1 inhibitor, as well as organs perfused with such perfusion fluids. One of ordinary skill in the art is familiar with standard organ perfusion fluids, including University of Wisconsin solution, Euro-Collins solution, BT01 solution, Ringer's lactate solution and normal saline solution. Other non-MEK1 inhibitor organ perfusion agents which can be added to the foregoing perfusion solutions include calcium entry blockers (e.g. lidoflazine), cytoprotectors (e.g., natriuretic factor, PG12, trimetazidine), free radical chelating agents and scavengers (e.g., allopurinol, mannitol, glutathione), and substrates for the mitochondrial respiratory chain (e.g., aspartate, glutamate).

EXAMPLES

Methods

Ischemia model

Adult male SV-129 mice (18–22g, Taconic Farms, Germantown, N.Y., USA) were housed under diurnal lighting conditions and allowed food and water ad libitum. Animals were anesthetized with 1.5% halothane and maintained in 1.0% halothane in 70% $N_2O$ and 30% $O_2$ using a Fluotec 3 vaporizer (Colonial Medical, Amherst, N.H., USA). Ischemia was induced with a 8.0 nylon monofilament coated with silicone resin/hardener mixture (Xantopren and Elastomer Activator, Bayer Dental, Osaka, Japan) as described previously (Huang et al., Science 265:1883–1885, 1994). For reperfusion, the filament was withdrawn, and the carotid artery was opened. In preliminary experiments, ddY mice underwent reperfusion more efficiently than ICR mice. In each mouse, regional cerebral blood flow (rCBF) was monitored by Laser-Doppler flowmetry (FLO-C1, Omegawave, Tokyo, Japan) using a flexible probe affixed to the skull (2 mm posterior and 6 mm lateral to the bregma). Core and temporal muscle temperature during surgery were recorded and maintained at ~37° C. as described. For 3 hours after surgery, the mice were monitored in a heating chamber at 32° C. (ThermoCare, Incline Village, Nev., USA). U0126 (Promega, Madison, Wis., USA) was dissolved in dimethyl sulfoximde (DMSO), frozen at –20° C. until use, and was prepared fresh by dilution in 0.1M PBS just before use. For treatment with U0126 or vehicle (0.1M PBS containing 0.4% DMSO) was injected into the femoral vein over a period of 10 seconds. For treatment with PD98059 or SB203580, or vehicle controls, two microliters of the agent or vehicle (PD98059, SB203580 or dimethyl sulfoxide (DMSO)) were injected i.c.v. (bregma –0.9 mm lateral, –0.1 mm posterior, –3.1 mm deep) 30 minutes before ischemia using a Hamilton injection syringe. Animal protocols followed the National Cardiovascular Center's guidelines for animal care and experiments.

Forebrain ischemia was induced by bilateral carotid artery occlusion (BCAO) in Mongolian gerbils (male, 50–70 g) under anesthesia with 1.0% halothane in 70% $N_2O$ and 30% $O_2$ using a vaporizer (Halowick, Muraco Medical, Tokyo, Japan). Rectal temperature during BCAO was kept at ~37° C. with a thermostat and a heating pad (NS-TC, Neuroscience, Tokyo, Japan, and BAT-12, Physitemp, N.J., U.S.A.), and monitored for 6 hours after reperfusion. For lesioning, the left temporal bone was drilled, and the cortical area ventral to the rhinal sulcus was electrically coagulated 7 days before BCAO.

Immunohistochemistry

Mice and gerbils were deeply anesthetized with an overdose of sodium pentobarbital (100 mg/kg i.p.) and then transcardially perfused with 0.9% saline solution followed by 4% paraformaldehyde in 0.1M phosphate-buffered saline (PBS) pH 7.4, or 4% paraformaldehyde in 0.1M PBS pH 7.4 respectively. The brains were quickly removed and stored in the same fresh buffer containing 20% sucrose. Brains were cut into coronal sections of 40 $\mu$m thickness on a freezing microtome (HM400R, Microm, Walldorf, Germany). The sections were processed by the free-floating method as described previously (Uemura et al., Brain Res. 542:343–347, 1991).

For immunohistochemical analysis, sections were treated in succession with primary antibody (1:100 for phospho-specific ERK1/2 antibody and 1:500 for anti-ERK2 antibody, respectively) and biotinylated goat anti-rabbit IgG (Vector Laboratories, Burlingame, Calf., USA). Immunoreactive products were detected by an avidin-biotin-peroxidase complex technique using 0.005% $H_2O_2$ and 3,3'-diaminobenzidine tetrahydrochloride (DAB; Sigma, St. Louis, Mo., USA) as a chromogen. For fluorescence double immunostaining with NeuN immunostaining, the sections were treated with phospho-specific ERK1/2 antibody and anti-Neuronal Nucleic (NeuN) monoclonal antibody (1:1000) (Chemicon International, Temecula, Calf., USA) then treated with biotin-conjugated goat anti-mouse IgG1 antibody (Southern Biotechnology Associates, Birmingham, Ala., USA) and Alexa Fluor 546 conjugated goat anti-rabbit antibody (Molecular Probes, Eugene, Oreg., USA). Then, the sections were treated with Alexa Fluor 488 conjugated streptavidin (Molecular Probes, Eugene, Oreg., USA). For fluorescence double staining with propidium iodide (Molecular Probes, Eugene, Oreg., USA), phospho-ERK1/2 immunostaining was labeled with Alexa Fluor 488 conjugated streptavidin. The sections were observed under an Olympus confocal laser microscope (FLUOVIEW, Tokyo, Japan).

Western blot analysis

For mouse tissues, ischemic and non-ischemic brains were dounce homogenized in 1 ml potassium phosphate buffer (10 mM $KPO_4$, pH7.05; 1 mM EDTA; 5 mM EGTA; 10 mM $MgCl_2$; 5 mM $\beta$-glycerophosphate; 1 mM sodium vanadate; 1 mM dithiothreitol [DTT]; 0.5% NP-40; 0.1% Brij-35). Lysates were clarified by centrifugation at 14,000 g for 10 minutes. The protein concentration in the supernatant was determined by the Bradford assay (Bio-Rad Laboratories, Hercules, Calif., USA). To test for phosphorylation of ERK1/2, 40 $\mu$g of total cell lysate was run on a 10% SDS-PAGE gel, transferred onto an Immobilon-P membrane [polyvinylidene fluoride (PVDF) membrane; Millipore Corp., Bedford, Mass., USA], and a Western blot was performed using phospho-specific p44/42 MAPK antibodies (1:1000) (New England Biolabs, Beverly, Mass., USA). Proteins were detected using enhanced chemiluminescent immunodetection (ECL; Amersham Life Sciences, Piscataway, N.J., USA). To analyze the protein levels within each lane, the blot was stripped and reprobed, according to Amersham Life Sciences manufacturer's instructions, using C-14 anti-ERK2 antibody (1:1000) (Santa Cruz Biotechnology, Santa Cruz, Calif., USA).

For gerbil tissues: dissected brain tissues were homogenized in 0.5 ml of potassium phosphate buffer as described above, followed by 10 minute centrifugation at 14,000×g. Thirty μof total cell lysate was analyzed by SDS-polyacrylamide gel electrophoresis (SDS-PAGE), and transferred onto Immobilon-P membrane (Millipore Corp. Bedford, Mass., USA). Western blotting was performed using phospho-specific ERK1/2 antibody, phospho-specific p38 protein kinase antibody, or phospho-specific JNK antibody (1:1000, respectively; New England Biolabs, Beverly, Mass., USA) and horseradish-peroxidase-conjugated anti-rabbit immunoglobulin G (IgG) (1:2000) (Dako, Glostrup, Denmark) in phosphate buffered saline (PBS) containing 3% bovine serum albumin and 0.1% Tween-20, sequentially. Immunoblots were visualized using ECL immunodetection system kit (Amersham, Arlington Heights, Ill., USA). To analyze protein levels of ERK1/2, the immunoblots were stripped and reprobed with anti-ERK1 and anti-ERK2 antibodies (1:2000, respectively) (Santa Cruz Biotechnology, Santa Cruz, Calif., USA). Immunoblots were scanned with an Epson Image Scanner, and the density was measured using NIH Image Analysis software (Ver. 1.54).

Analysis of brain function

Twenty-two hours after reperfusion, mouse and gerbil brains were removed and sliced into five coronal sections of 2 mm thickness using a mouse brain matrix (RBM-2000C; Activational System, Mich., USA). Brain slices were treated with 2% 2,3,5-triphenyltetrazoliumn chloride (Sigma Chemicals, St. Louis, Mo., USA), followed by 10% formalin overnight as described previously (Bederson et al., *Stroke* 17:1304–1308, 1986). In the mouse tissues, the infracted areas, outlined in white, were measured by an image analysis system (MCID ver. 3, Imaging Research, Inc., Ontario, Canada) on the posterior surface of each section and infarction volume was calculated by summing the infarction volume of sequential 2-mm thick sections. For evaluation at 72 hr after reperfusion, the mice were deeply anesthetized with an overdose of pentobarbital and transcardially fixed with 30 ml of 10% formalin in 0.1M PBS. The brains were quickly removed and saturated with 20% sucrose. Fifty-micrometer-thick coronal sections were cut on a freezing microtome, and every 20th section from the frontal pole was mounted on a glass slide and stained with 0.05% thionin. A coverslip was applied with Paramount (Sigma, St. Louis, Mo., USA), and the infarction areas were measured as described above and quantitated by summing the infarction areas of 6 sequential sections. The data were analyzed by standard statistical methods.

For the gerbil tissues, the infarcted areas, outlined in white, were measured on the posterior surface of each section by an image analysis system (Olympus, Tokyo, Japan) and infarction volume was calculated by summing the infarct areas. Correction for brain swelling was done by calculating using the following formula: (contralateral volume−ipsilateral undamaged volume)×100/contralateral volume (see Swanson et al, *J. Cereb. Blood Flow Metab.*, 10, 290–293, 1990).

Evaluation of hippocampal injury in gerbils

Seven days after reperfusion, the brains were removed and cut into coronal sections of 40 μm thickness using the freezing microtome as described above. The brain sections were mounted on glass slides and stained with 0.1% cresyl violet. The viable CA1 pyramidal cells were counted under an Olympus microscope using a ×40 objective lens and expressed as cells/mm.

Statistics

Data are presented as mean ±SEM Data were analyzed by Student-t test or one-way ANOVA followed by Bonferroni's post hoc test. For neurological score Mann-Whitney U-test was used. $p<0.05$ was considered statistically significant.

Physiology

In randomly selected mice (n=5,200 μM PD98059; n=4, 0.4% DMSO), regional cerebral blood flow (rCBF) was measured by Laser-Doppler flowmetry (PF2B, Perimed, Stockholm, Sweden) using a flexible 0.5-mm fiber optic extension to the masterprobe. The tip of the probe was secured 2 mm posterior and 6 mm lateral to the bregma on the ipsilateral hemisphere in animals. Steady-state baseline values were recorded before MCA occlusion, and rCBF during and after occlusion was expressed as percentage of the baseline values. RCBF and arterial blood pressure were monitored using MacLab/8 data acquisition system (AD Instruments, Milford, Mass., USA) equipped with an ETH 400 transducer amplifier via femoral artery catheterized with a PE-10 polyethylene tubing. Arterial blood samples (50 μl) were analyzed for pH, oxygen ($pO_2$) and carbon dioxide ($pCO_2$) using a blood gas/pH analyzer (Coming 248, Ciba-Corning Diagnostics, Medford, Mass., USA). Core temperature was maintained at approximately 36.5° C. with a thermostat (FMC Corp., Brunswick, Me., USA) and a heating pad (Watlow, St. Louis, Mo., USA) during MCA occlusion, and the mice were kept in a warmer (Thermocare, Incline Village, N.J., USA) for 3 hours after reperfusion.

Example 1

ERK Activation Following Ischemia

A mouse model of cerebral ischemia was employed to examine the role of the ERK/MAP kinase pathway following ischemia. Cerebral ischemia was induced in SV-129 mice by transient middle cerebral artery (MCA) occlusion for the times given below. Blood flow was restored to assess the effects of reperfusion. Western blot analysis was performed on lysates (40 μl per lane) from the contralateral (C) and ipsilateral/ischemic (I) sides of the brain following 1 hour ischemia (II) followed by 3 minutes reperfusion (3R) or 2 hour ischemia (2I) followed by 3 minutes reperfusion (3R). ERK2 phosphorylation was increased after 60 or 120 minutes of ischemia followed by 3 minute reperfusion (FIG. 1, upper panel). Amounts of ERK1/2 protein were detected using ERK-specific antibodies (FIG. 1, lower panel).

Figure 2:
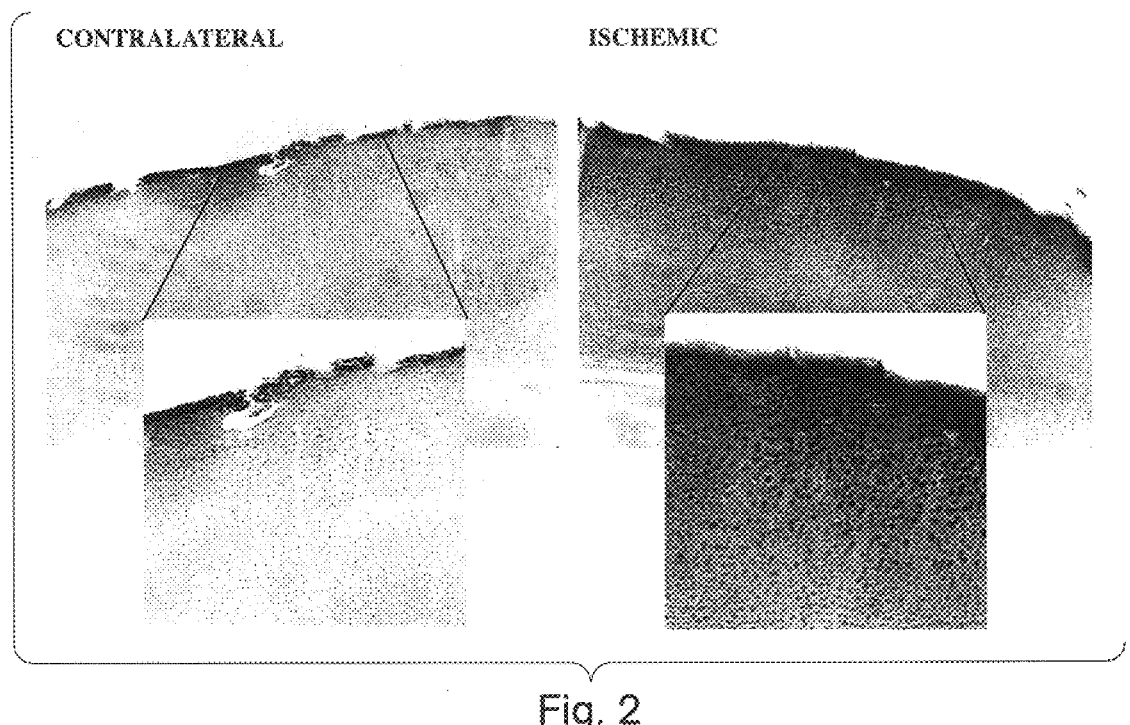
FIG. 2 shows the immunohistochemistry of phosphorylated ERK1/2 in brain slices following ischemia and reperfusion.

Immunohistochemistry of brain sections (40 μm thickness) was performed using a phospho-specific ERK1/2 antibody (New England Biolabs, Beverly, Mass.) showed an increase of phosphorylated ERK in the nucleus of cortical cells in the ischemic core, after 60 minutes ischemia and 3 minutes reperfusion (FIG. 2). Contralateral (non-ischemic) and ischemic (ipsilateral) sides of the brain are indicated; magnification was 100×.

Example 2

Inhibition of MEK1 Activity Reduces Ischemia/Reperfusion Damage

MEK1 activates the MAP kinases ERK1 and ERK2 by specific phosphorylation. To evaluate the role of MAP kinase activation in neuronal cell damage, the MEK1-specific inhibitor PD98059 (New England Biolabs, Beverly, Mass., USA) was used to selectively inhibit MEK1 without generally inhibiting other kinases. To inhibit MEK1 in the mouse stroke model, 2 μl of 200 μM PD98059 was injected into the cerebral ventricle 30 minutes prior to the induction of focal cerebral ischemia. The control animals were injected likewise with 0.4% DMSO. Following 120 minutes ischemia and 3 minutes reperfusion, immunohistochemistry using the phospho-specific ERK1/2 antibody used in Example 1 demonstrated that phosphorylation of ERK1/2 was reduced in the middle cerebral artery territory in mice pretreated with PD98059 (FIG. 3).

Figure 4A:
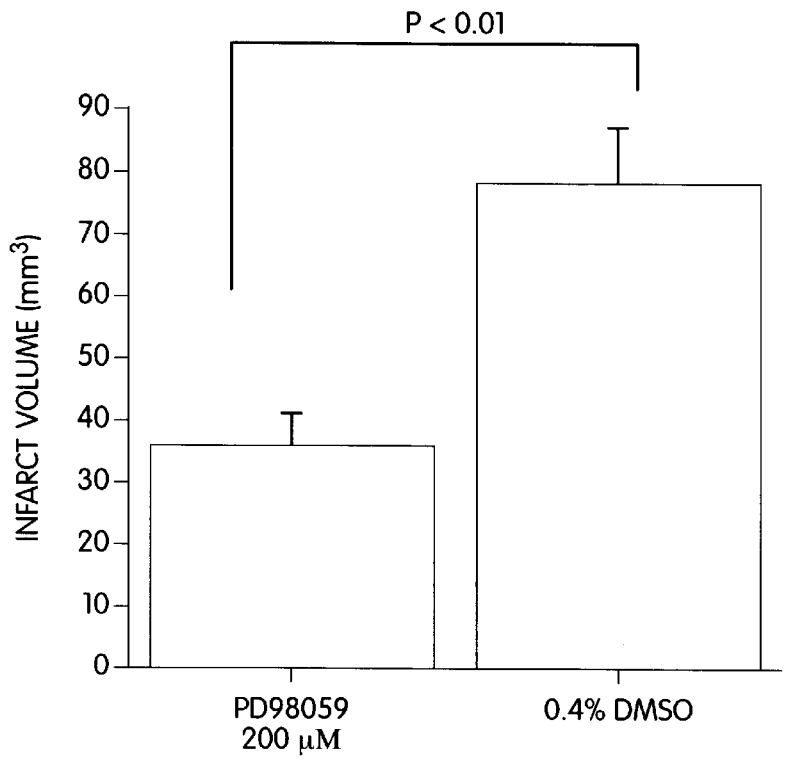
FIGS. 4A, B and C are graphs which show the effect of PD98059 on infarct volume.
Figure 4B:
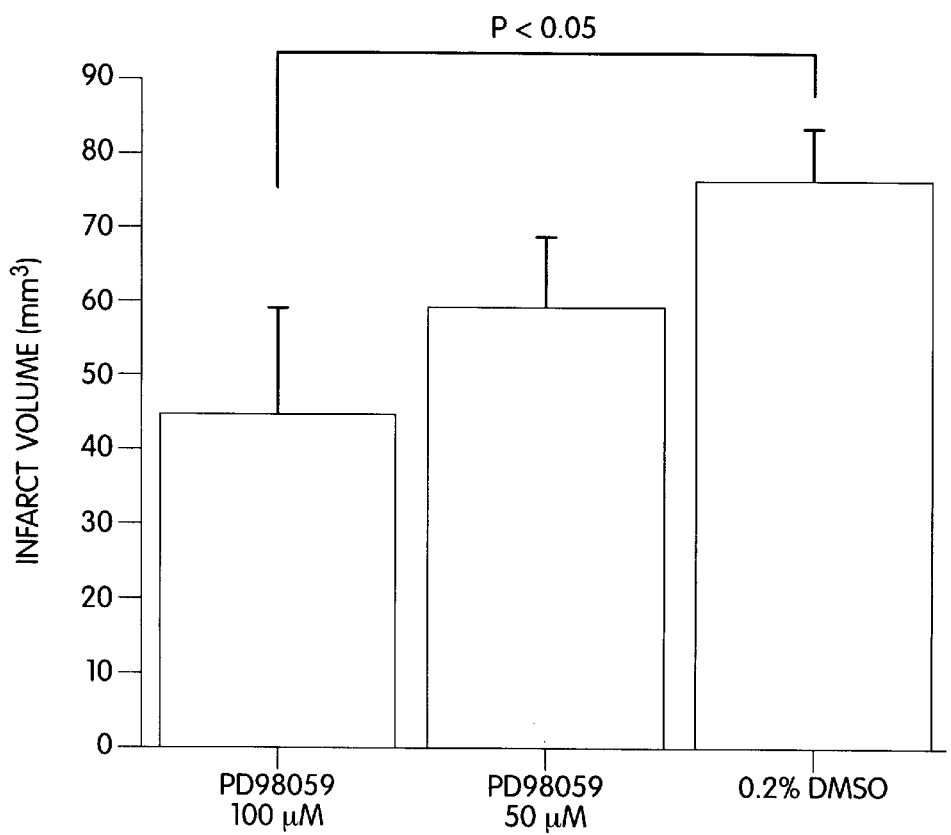
Figure 4C:
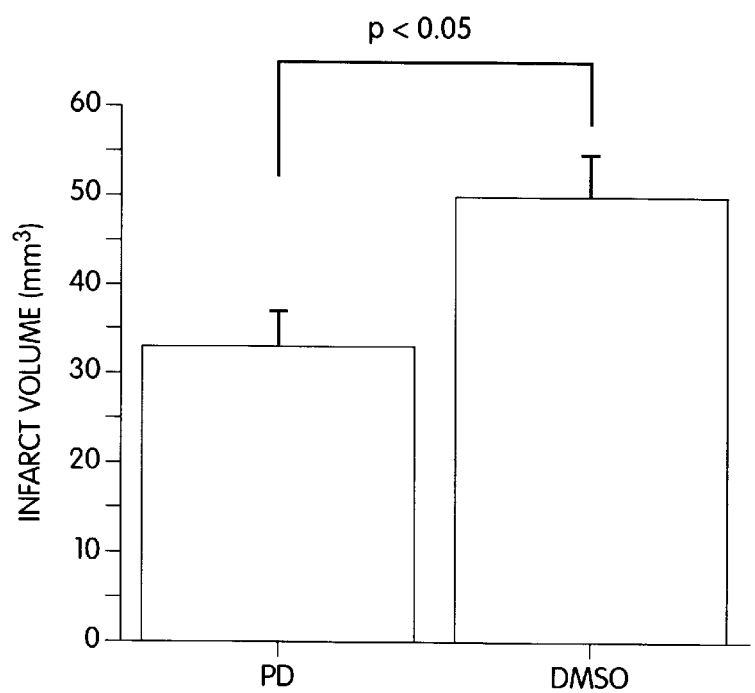

To analyze if PD98059 was a neuroprotective agent, the damage induced by focal cerebral ischemia was assessed using the tetrazolium chloride (TTC) staining method (Bederson et al., *Stroke* 17:1304–1308, 1986). Mice that were pretreated with 200 μM PD98059 as above showed a 55% (P<0.01) decrease in total damage as determined 22 hours following focal cerebral ischemic insult (FIG. 4A). The neuroprotective ability of the drug is dose-dependent, with a 42% (P<0.05) and a 23% (P<0.05) decrease in total damage observed when mice were pretreated with 100 μM and 50 μM of PD98059, respectively (FIG. 4B). Animals that received 200 μM PD98059 showed a 43% (P<0.05) decrease in total damage three days post-ischemia (FIG. 4C).

Neurological deficits also were significantly attenuated in animal pretreated with PD98059. Neurological deficits caused by ischemia were scored according to Huang et al. (*Science* 265:1883–1885, 1994). Neurological grading three days after 2 hours of MCA occlusion and reperfusion was 0.71±0.29 (SEM) and 2.2±0.3 (P<0.05) in PD98059-treated and vehicle-treated mice, respectively. These data indicate that the inhibition of the MEK1/ERK pathway has long-term neuroprotective significance.

Example 3
Inhibition of MEK1 Activity Does Not Alter Physiological Parameters

To determine if the administration of PD98059 affected the physiology of the treated animals, several physiological parameters were measured.

Regional cerebral blood flow (rCBF) was determined in the presence of absence of 200 μM PD98059 (Table 1). rCBF was determined by Laser-Doppler flowmetry (PF2B, Perimed, Stockholm, Sweden) during 2 hours of middle cerebral artery occlusion and 30 minutes of reperftision in PD98059 treated and DMSO control treated groups under 1% halothane anesthesia. Data are presented as means ±SD. Therefore, the decrease in ERK1/2 phosphorylation seen with PD98059 was not due to higher blood flow.

TABLE 1

| | Regional CBF | |
|---|---|---|
| | PD98059 (n = 5) | DMSO (n = 4) |
| RCBF (during MCA) | 15.9% ± 1.7 | 25.2% ± 5.7 |
| RCBF (after MCA) | 94.9% ± 8.9 | 102.5% ± 6.8 |

Mean arterial blood pressure (MABP) was determined in the presence or absence of 200 μM PD98059 10 minutes before and 1 hour after induction of ischemia, and 30 minutes after reperfusion under 1% halothane anesthesia (Table 2). Data are presented as means±SD. MABP was determined to be unaltered.

TABLE 2

| | Mean arterial blood pressure | |
|---|---|---|
| | PD98059 (n = 5) | DMSO (n = 4) |
| MABP (before) | 86.4 ± 10.9 | 80.7 ± 7.5 |
| MABP (during) | 81.8 ± 4.1 | 82.3 ± 2.1 |
| MABP (after) | 86.0 ± 12.3 | 82.8 ± 13.5 |

Partial oxygen tension ($pO_2$), partial carbon dioxide tension ($pCO_2$), and blood pH were determined in the presence or absence of 200 μM PD98059, 1 hour after the induction of ischemia under 1% halothane anesthesia (Table 3). Data are presented as means ±SD. $pO_2$, $pCO_2$, and blood pH did not differ between the two groups.

TABLE 3

| | Physiological variables | |
|---|---|---|
| | PD98059 (n = 5) | DMSO (n = 4) |
| PH | 7.32 ± 0.07 | 7.32 ± 0.06 |
| $PCO_2$ | 49.9 ± 3.5 | 48.8 ± 5.1 |
| $PO_2$ | 139.1 ± 21.6 | 155.3 ± 13.8 |

Body temperature was unaltered up to 22 hours after reperfusion in the PD98059-treated animals when compared to the vehicle-treated controls, with values of 34.6±0.8° C. and 35.9±0.4° C., respectively. In addition, temporal muscle temperature, reflective of head temperature, was unaltered up to three hours after reperfusion in the PD98059-treated animals when compared to the vehicle-treated controls, with values of 35.5±0.1° C. and 35.2±0.3° C., respectively.

The specificity of PD98059 was next evaluated by analyzing whether the stress-induced p38 MAP kinase and SAPK/JNK pathways are mediators of tissue injury in the focal ischemia/reperfusion model. No detectable increase in phosphorylated p38 MAP kinase or phosphorylated c-Jun (a substrate for SAPKs/JNKs) was observed by Western blot analysis and immunohistochemistry using phospho-specific p38 and phospho-specific c-Jun antibodies (New England Biolabs, Beverly, Mass., USA).

The effect of an inhibitor of these pathways also was determined. SB203580, an inhibitor of p38 MAP kinase (1–2 μM) and SAPKs/JNKs (>10 μM), was administered to animals as described above for PD98059. Two microliters of 100 μM SB203580 or 0.2% DMSO were injected into the lateral ventricle 30 minutes prior to ischemia. SB203580 did not protect the brain from injury relative to vehicle-treated controls as determined by infarct measurement. Thus, the protection observed with PD98059 is due to its specific inhibition of the MEK1/ERK pathway.

Example 4
Inhibition of MEK1 Activity by U0126 Reduces Ischemia/ Reperfusion Damage and Protects Against Glutamate Toxicity or Hypoxia The experiments below demonstrate that U0126, a novel MEK-specific inhibitor, profoundly decreased infarct volume by delayed intravenous systemic administration, and that U0126 dramatically protected neurons against glutamate toxicity or hypoxia in vitro and in vivo.

MEK1 Inhibitors Protect HT22 Cells Against Glutamate Oxidative Injury

Several MAP kinase inhibitors were tested in HT22 cells exposed to high concentrations of extracellular glutamate (5 mM). High concentrations of extracellular glutamate initiate oxidative glutamate toxicity (Davis and Maher, *Brain Res.* 652:169, 1994), which is considered as distinct from glutamate excitotoxicity mediated by glutamate receptors (Choi, *Neuron* 1:623, 1988). Excessive amounts of extracellular glutamate prevents cystine uptake into the cells, resulting in the depletion of intracellular cystine followed by the loss of glutathione. Glutathione depletion induces excess amount of reactive oxygen species which are deleterious to cells. This experimental paradigm serves as a good model in vitro to study the molecular events in neuronal injury (Davis and Maher, 1994; Murphy et al., *FASEB J.* 4:1624, 1990).

Mouse hippocampal HT22 cells are derived from the HT4 cell line (Morimoto and Koshland, *Neuron* 5:875, 1989) and were maintained in 75-cm$^2$ flasks (FALCON) using Dulbecco's Modified Eagle (DME) medium supplemented with 5% (v/v) of heat-inactivated (56° C., 30 min) horse serum [Life Technologies (GIBCO/BRL), Rockville, Md., USA] and 5% (v/v) of precolostrum newborn calf serum (Mitsubishi Kasei Institute of Life Sciences, Mitsubishi Chemical Corporation, Tokyo, Japan) (5/5 DME). The viability of HT22 cells was determined in 24-well plates by either visual cell counting or by using the method of 3-(4,5-dimethylthiazol-2-yl)-2,5-diphenyl tetrazolium bromide reduction (MTT assay; T. Mosmann, *J. Immunol. Methods* 65: 55, 1983). Cells were dissociated and seeded into 24-well plates at a density of 3×10$^5$ cells per well in 500 μl medium. The following day cells were exposed to 5 mM glutamate with or without several different concentrations of MAP kinase inhibitors. Morphological changes were monitored and cell injury was determined by the MTT assay. Twenty four hours after the treatment, MTT solution (I mg/ml) was added to each well and incubated for 1 hour. An equal volume of solubilization solution (50% dimethylformamide, 29% SDS, pH 4.8) was added to the wells, and the absorption value at 540 nm was measured by using Titertek Twinreader (Flow Laboratories, McLean, Va., USA).

Cell injury started 8 hours after addition of glutamate, and was completed by 10 hours (Fig. 5A). Pretreatment with SB203580 (50 μM), an inhibitor of p38 MAP kinase (1–2 μM) and SAPKs/JNKs (>10 μM) (Cohen, *Trends Cell Biol.* 7:353, 1997), did not protect HT22 cells (FIGS. 5B, C). PD98059, a MEK1 inhibitor, partially attenuated cell injury 9 hours after glutamate addition (FIG. 5B), however, these protective effects did not sustain for 24 hours (FIG. 5C). On the contrary, U0126, a MEK-specific inhibitor, that, unlike PD98059, can inhibit activated MEK1, dramatically inhibited cell injury (FIGS. 5B, C). The cytoprotection with U0126 was dose-dependent, and complete inhibition of cell injury was achieved at 10 μM (FIG. 5D), a concentration that specifically inhibits MEK1. U0126 has not been shown to affect other protein kinases than MEK1/2 under 30 μM (Favata et al., 1998; DeSilva et al., *J. Immunol.* 160:4175, 1998). U0126 was shown not to be toxic at concentrations up to 10 μM (FIG. 5D).

It next was determined whether MEK1 is activated in oxidative glutamate injury in HT22 cells. Phosphorylation of ERK1/2 in HT22 cells was examined after glutamate addition. Collected culture tissues were homogenized in I ml of potassium phosphate buffer [10 mM KPO$_4$ (pH 7.05), 11 mM EDTA, 5 mM EGTA, 10 mM magnesium chloride, 50 mM β-glycerophosphate, 1 mM sodium vanadate, 1 mM dithiothreitol (DTT), 0.5% NP-40, 0.1% Brij-35], and centrifuged 10 min at 14,000×g. Protein concentration in the supernatant was determined by the Bradford assay (Bio-Rad Laboratories, Hercules, Calif., USA). To evaluate phosphorylation of ERK1/2, 40 μg of total protein of each sample was loaded on a 10% SDS-PAGE gel, electrophoresed, and transferred onto Immobilon-P membrane (Millipore Corp., Bedford, Mass., USA). Western blotting was performed using phospho-specific ERK1/2 MAPK antibody (1:1000) (New England Biolabs, Beverly, Mass.) and horseradish-peroxidase-conjugated anti-rabbit immunogloblin G (IgG) (1:1000) (Santa Cruz Biotechnology, Santa Cruz, Calif.) in phosphate buffered saline (PBS) containing 3% bovine serum albumin and 0.1% TWEEN™-20, sequentially. Imrunoblots were visualized using ECL immunodetection system kit (Amersham, Arlington Heights, Ill., USA). To analyze protein levels of ERK1/2, the immunoblot was stripped and reprobed with anti-ERK 1/2 antibody (1:1000) (New England Biolabs, Beverly, Mass., USA).

While basal levels of phosphorylated ERK1/2 were observed in HT22 cells, phosphorylation of ERK1/2 further increased 7 to 8 hours after glutamate addition. Preincubation with U0126 (10 μM) completely blocked phosphorylation of ERK1/2 (FIG. 5E). Thus, these data strongly indicate that U0126 protects HT22 cells by inhibiting phosphorylation of ERK1/2 against oxidative glutamate injury, and that ERK1/2 activation under the unstimulated condition may not contribute to cell survival at least in HT22 cells.

The cytoprotective effects of delayed treatment with U0126 after glutamate addition were then tested. Surprisingly, application of 10 μM of U0126 initiated up to 7 hours after addition of glutamate completely inhibited cell injury, which started 8 hours after glutamate addition (FIG. 5F).

Figure 6A:
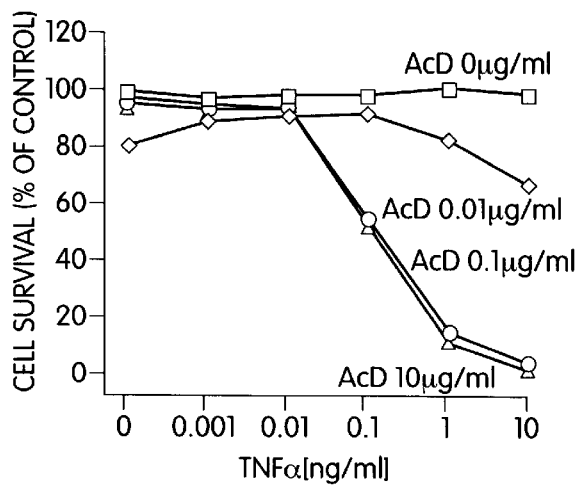
FIG. 6 shows that MEK1 inhibition with U0126 does not block cell death induced by either TNF$\alpha$ plus actinomycin D or calcium ionophore A23187. Cell injury was assessed by the MTT assay after 24 hours of incubation. (A) Cotreatment with TNF$\alpha$ (R & D Systems) and actinomycin D (AcD; open squares, 0 $\mu$g/ml; open diamonds, 0.01 $\mu$g/ml; open circles, 0.1 $\mu$g/ml; open triangles, 10 $\mu$g/ml; Wako) induces death in HT22 cells. Data are from 2 independent experiments. (B) Pretreatment with 10 $\mu$M of U0126 does not inhibit death in HT22 cells after incubation with TNF$\alpha$ plus actinomycin D (0.1 $\mu$g/ml). Percent cell survival is presented as mean±SEM (n=4). (C) Incubation for 24 hours with A23187 (Wako, >300 nM) induces death in HT22 cells. Data are from a representative experiment of 2 independent experiments. Percent cell survival is presented as mean±SEM (n=4). (D) Pretreatment with U0126 (5 or 10 $\mu$M) does not inhibit death in HT22 cells after incubation for 24 hours with A23187 (300 nM). Data are from a representative experiment of 2 independent experiments. Percent cell survival is presented as mean ±SEM (n=4).
Figure 6B:
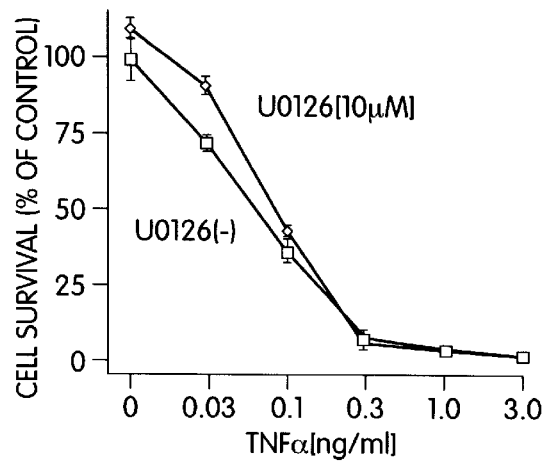
Figure 6C:
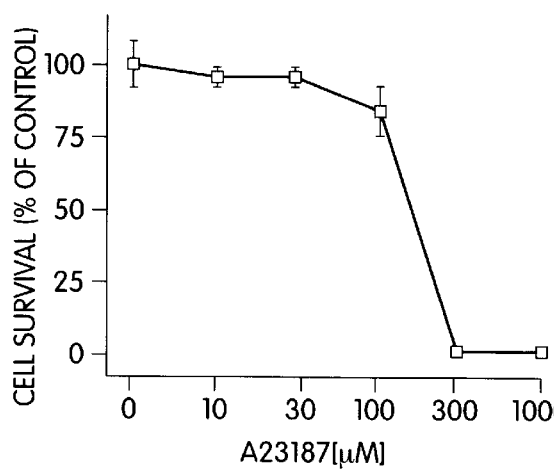
Figure 6D:
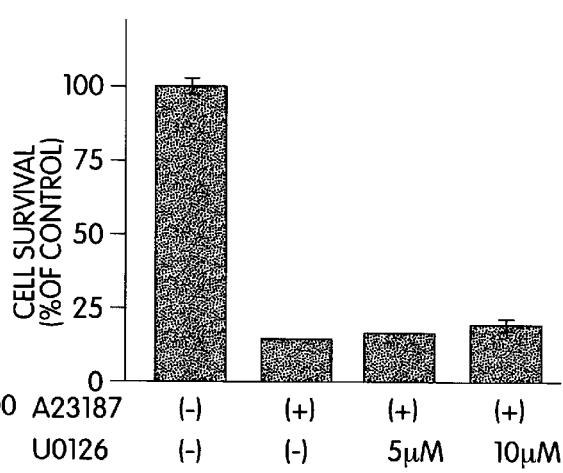

To examine whether MEK is involved in cell injury induced by other stimuli, U0126 was tested in HT22 cells treated with TNFα and actinomycin D. Neither TNFα nor actinomycin D induced death in HT22 cells; however, a combination of both TNFα (>1 ng/ml) and actinomycin D (>0.1 μg/ml) killed HT22 cells after incubation for 24 hours (FIG. 6A). As reported in other cells, treatment with TNFα plus actinomycin D induces cell shrinkage and chromatin condensation in HT22 cells, which are typical for apoptosis (data not shown; Gillio Tos, et al., *Blood* 87:2486, 1996). U0126 (10 μM) did not protect HT22 cells against TNFα and actinomycin D induced cell death (FIG. 6B). To ask whether actinomycin D could mask the cytoprotective effect with U0126 by inhibiting transcription which might be necessary for the protective efficacy of U0126, U0126 was tested in HT22 cells exposed for 24 hours to the calcium ionophore A23187 (300 nM). A23187 induced extensive cell death in HT22 cells at 300 nM (FIG. 6C). U0126 did not protect HT22 cells against A23187 (FIG. 6D). Furthermore, U0126 did not protect HT22 cells against staurosporine, a nonselective kinase inhibitor (1 μM) (data not shown). Therefore, cytoprotection by U0126 is dependent upon the specific cell death stimuli.

U0126 Protects Primary Cortical Neurons Against Glutamate as Well as Hypoxia

To ask whether U0126 can inhibit neuronal cell injury, primary cultured cortical neurons harvested from rat embryos (Yamada et al., *Eur. J. Neurosci.* 7:2130, 1995) were subjected to glutamate (5 mM) toxicity (Murphy et al., 1990) or hypoxia for 8 hours. The cortex was dissected from embryonic 20 day old (E20) rat brain (Wistar ST, both sexes; Nippon SLC, Hamamatsu, Japan). The tissue fragments were added to 10 ml of fresh $Ca^{2+}$, $Mg^{2+}$-free phosphate buffered saline, containing papain (90 unit), DNAse 1 (2000 unit), DL-cysteine (2 mg), recrystallized bovine serum albumin (2 mg) and glucose (50 mg), then incubated 30 min at a constant rotation of 200 rpm in a 37° C. incubator. After papain digestion, the tissue fragments were resuspended in DME medium containing 3 nM selenium chloride and 1.9 mg/ml sodium bicarbonate, supplemented with 5% of precolostrum newborn calf serum (Mitsubishi Kasei Institute of Life Sciences, Mitsubishi Chemical Corporation, Tokyo, Japan) and 5% of heat-inactivated horse serum. The dissociated cells were then immediately plated at a density of 3×10$^2$ cells/cm$^2$ on polyethyleneimine-coated 24 well plates (FALCON). The cells were incubated in 5% $CO_2$ and 20% $O_2$ in a $CO_2$ incubator at 37° C. for one day (oxidative glutamate toxicity) or 4 days (hypoxia-reoxygenation). For the hypoxia experiments, the cultures were transferred on the fifth day in vitro to a hypoxic chamber (APCW-36, ASTEK, Fukuoka, Japan). The cultures were kept in the chamber for 8 hours (37° C., $O_2$<0.2% and 5% $CO_2$), and then transferred to normoxia condition (5% $CO_2$ and 20% $O_2$) for 24 hours.

Figure 7A:
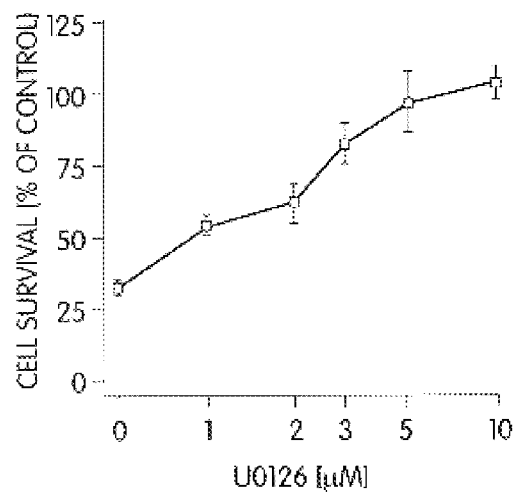
FIG. 7 shows that MEK inhibition with U0126 protects rat primary cortical cultures against glutamate toxicity as well as hypoxia. (A,B) Neuronal survival was determined by visual counting of microtuble-associated protein 2 (MAP2) immunostained cells 24 hours after glutamate addition (A) or hypoxic challenge (B). (A) Dose-dependent protective effects of U0126 in cortical neurons exposed to 5 mM glutamate for 24 hours. (B) The protection with U0126 against hypoxia for 8 hours is dose-dependent in primary cortical cultures assessed 24 hours after reoxygenation. (C–H) Fluorescent photomicrographs of MAP2 immunostained neurons in primary cortical cultures before (C, D) or after 24 hours of reoxygenation following hypoxia for 8 hours (E–H) with [D, H, 10 $\mu$M; F, 1 $\mu$M; G, 3 $\mu$M] or without (C, E) incubation of U0126. (E) Note that the number of MAP2 immunostained neurons are extensively decreased in the cultures subjected to hypoxia. (H) On the contrary, neurons pretreated with 10 $\mu$M of U0126 show perikaryal integrity, however, the dendrites are fragmented after hypoxia. Bars, 60 $\mu$m.
Figure 7B:
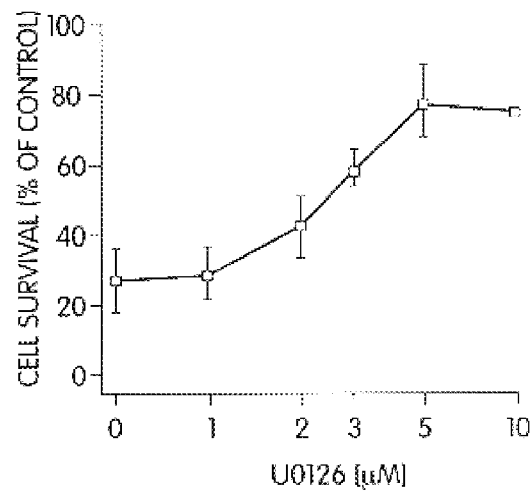
Figure 7C:
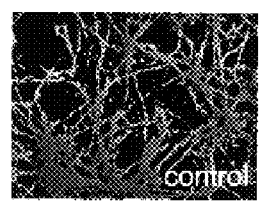

Pretreatment with U0126 protected primary cortical cultures in a dose-dependent manner against both glutamate toxicity and hypoxia assessed by counting the number of microtuble-associated protein 2 (MAP2) immunostained cells (FIGS. 7A and B). The viability of primary cortical cultures was determined by visual counting of microtubule-associated protein 2 (MAP 2) immunostained cells. MAP 2 immunostaining was performed by sequential incubation with primary antibody against MAP 2 (Mouse monoclonal, e.g., Boehringer Mannheim(Roche Molecular BioChemicals, Indianapolis, Ind., USA); United States Biological, Swampscott, Mass., USA) and biotinylated anti-mouse IgG secondary antibody (Vector Laboratories, Burlingame, Calif., USA), and Cy3-conjugated streptavidin (Jackson ImmunoResearch Laboratories, West Grove, Pa., USA). The stained plates were observed under a Olympus fluorescence microscope (IX70) with excitation wave length and emission wave length of 530 nm and 590 nm, respectively. Results are expressed relative to the controls.

Figure 7D:
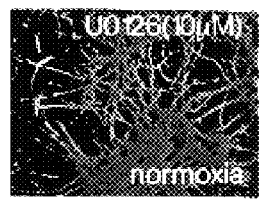
Figure 7E:
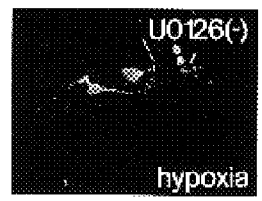
Figure 7F:
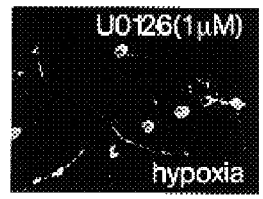
Figure 7G:
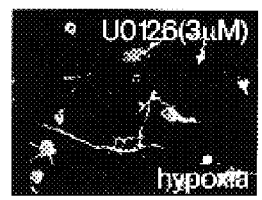
Figure 7H:

U0126 was not toxic in primary cortical neurons up to 10 $\mu M$ (FIG. 7D). Interestingly, immunostaining using MAP2 antibody revealed perikaryal integrity in U0126 (10 $\mu M$) treated cultures after hypoxia, however, the dendritic processes were fragmented (FIG. 7H). Thus, the data indicate that MEK-mediated cell death is also involved in terminally differentiated neuronal cells.

Delayed Intravenous Systemic Administration of U0126 Protects Brain Against Focal Cerebral Ischemia Induced by Permanent As Well As Transient Middle Cerebral Artery Occlusion in Mice The feasibility of MEK inhibition with U0126 as a therapeutic intervention for the treatment of stroke was investigated in a standard animal model. The mouse focal ischemia model induced by permanent as well as transient middle cerebral artery occlusion (MCAO) was employed. Focal cerebral ischemia was induced by permanent or transient MCAO using silicon/resin coated 8-0 nylon filament in ICR or ddY mice (male, 20–22g; SLC Japan), respectively, as described (Hara et al., 1997; Ma et al., 1998). In the preliminary experiments, it was found that ddY mice gained better reperfusion than ICR mice. Mice were anesthetized with 1.0% halothane in 70% $N_2O$ and 30% $O_2$ as described using a vaporizer (Halowick, Muraco Medical, Tokyo, Japan). In each mouse, regional cerebral blood flow (rCBF) was monitored by Laser-Doppler flowmetry (FLO-C1, Omegawave, Tokyo, Japan) using a flexible probe. The tip of the probe was affixed to the skull (2 mm posterior and 6 mm lateral to the bregma) with cyanoacrylate glue (Aron Alpha, Toa, Tokyo, Japan). Core and temporal muscle temperature during surgery were recorded and maintained at 37° C. with a thermostat and a heating pad (NS-TC, Neuroscience, Tokyo, Japan, and BAT-12, Physitemp, N.J., USA). Animals were monitored in an incubator at 32° C. for 6 hr after surgery. Experimental procedures were approved by the National Cardiovascular Center's Committee on Research. U0126 was dissolved in 0.1M phosphate buffered saline (PBS) containing 0.4% DMSO freshly just before use. For systemic administration, 100 $\mu l$ of the PBS containing U0126 was injected into the left femoral vein in mice.

Figure 8A:
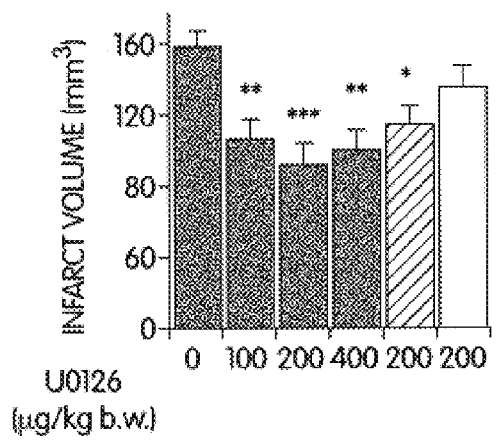
FIG. 8 indicates that intravenous systemic administration of U0126 protects against damage resulting from permanent as well as transient middle cerebral artery occlusion (MCAO) in mice. (A) ICR mice were subjected to permanent MCAO, and brain infarct volume was determined by triphenyltetrazolium chloride (TTC) staining 24 hr after induction of MCAO. U0126 was given 10 min before (blackened columns), 1 hr (dotted column) or 3 hr (white column) after MCAO. Single injection of U0126 before or 1 hr after MCAO was protective (ANOVA followed by Bonferroni). Single asterisk, P<0.05; double asterisks, P<0.01; triple asterisks, P<0.001 compared with the vehicle-injected group. Data are presented as mean+SEM (n=8–11). (B) ddY mice were subjected to 3 hr of MCAO, and brain infarct was analyzed by TTC staining 24 hr after reperfusion. DMSO or U0126 (200 $\mu$g/kg) was administered intravenously at 2 hr and 50 min after induction of MCAO and 10 min before reperfusion. Significant protection was seen in both the cortex and subcortex in the U0126-treated mice (hatched columns) compared with DMSO-treated (white columns) (unpaired Student-t test). Data are presented as mean+SEM (n=12 in each group). Single asterisk, P<0.05; double asterisks, P<0.01. (C, D) Immunoblotting (c) and immunostaining (D) using phospho-ERK1/2 antibody show that intravenous administration of U0126 (200 $\mu$g/kg) 10 min before reperfusion diminishes phospho-ERK1/2 immunoreactivity in the damaged brain 5 min after reperfusion following 3 hr of MCAO. C, contralateral; I, ipsilateral. Scale bar: 200 $\mu$m.

Intravenous administration of U0126 10 minutes before permanent MCAO dramatically decreased infarct volume determined by 2,3,5-triphenyltetrazolium chloride (TTC) staining 24 hours after ischemia. Brains were removed and cut into coronal slices using a mouse brain matrix (Neuroscience, Tokyo, Japan). The sections were incubated with 2%, 2,3,5-triphenyltetrazolium chloride (Sigma), followed by 10% formalin overnight as described previously (Bederson et al. *Stroke* 17:472,1986). The infarcted areas, outlined in white, were measured on the posterior surface of each section by an image analysis system (Olympus, Tokyo, Japan) and infarction volume was calculated by summing the infarction areas. Maximum protection was achieved with 200 $\mu g/kg$ of U0126 (by 42%, P=0.0008) (FIG. 8A). Neurological deficits 24 hours after ischemia were improved by U0126 (Table 4). U0126 administration 1 hour after induction of permanent MCAO was still effective (by 27%, P=0.04), but not when given 3 hours after MCAO, although a decrease in infarct volume by 13.9% (P=0.29) was observed (FIG. 8A). Thus, the therapeutic temporal window for U0126 in permanent focal cerebral ischemia is about 1 hour in mice. U0126 did not affect regional cerebral blood flow (rCBF) and core temperature (Tables 4 and 5). Therefore, the brain protection was not due to altered physiological parameters, but was likely due to the neuroprotective efficacy of MEK inhibition by U0126, which further supports the in vitro data.

TABLE 4

Physiological parameters and neurological deficit score

| Treatment | n | Core Temp., ° C. | T.M. Temp., ° C. | RCBF, % | Neurological Score |
|---|---|---|---|---|---|
| DMSO (0.4%) | 8 | 37 0 ± 0.1 | 37.3 ± 0.2 | 15.0 ± 2.0 | 1.5 ± 0.3 |
| U0126 (100 $\mu g/kg$) | 9 | 37.0 ± 0.0 | 37.1 ± 0.1 | 13.5 ± 1.1 | 0.6 ± 0.2* |
| U0126 (200 $\mu g/kg$) | 9 | 36.9 ± 0.1 | 37.5 ± 0.2 | 17.0 ± 1.4 | 0.6 ± 0.2* |
| U0126 (400 $\mu g/kg$) | 11 | 37.0 ± 0.1 | 37.3 ± 0.1 | 17.4 ± 0.7 | 0.5 ± 0.2* |

Results are mean±SEM Temp., Temperature; T.M., Temporal Muscle.

Data for temperatures and rCBF were collected at 30 min after induction of middle cerebral artery occlusion (MCAO) in ICR mice. Neurological scoring was determined according to Hara et al., J. Cereb. Blood Flow Metab. 16: 605611 (1996), and performed just before the mice were killed at 24 h after MCAO. *, p<0.05 by Mann-Whitney U-test compared with DMSO.

TABLE 5

Changes in rectal temperature after 3.5 min BCAO in the gerbil

| Treatment | n | BCAO (° C.) | Reperfusion (° C.) | 1 h (° C.) | 3 h (° C.) | 6 h (° C.) |
|---|---|---|---|---|---|---|
| DMSO (0.4%) | 6 | 37.4 ± 0.1 | 37.8 ± 0.2 | 38.6 ± 0.2 | 37.9 ± 0.2 | 38.4 ± 0.3 |
| U0126 (50 $\mu g/kg$) | 7 | 37.4 ± 0.2 | 38.0 ± 0.2 | 39.0 ± 0.3 | 37.6 ± 0.3 | 38.4 ± 0.2 |
| U0126 (100 $\mu g/kg$) | 7 | 37.5 ± 0.1 | 38.0 ± 0.3 | 39.1 ± 0.5 | 38.3 ± 0.4 | 38.5 ± 0.1 |

Results are mean±SEM

Figure 8B:
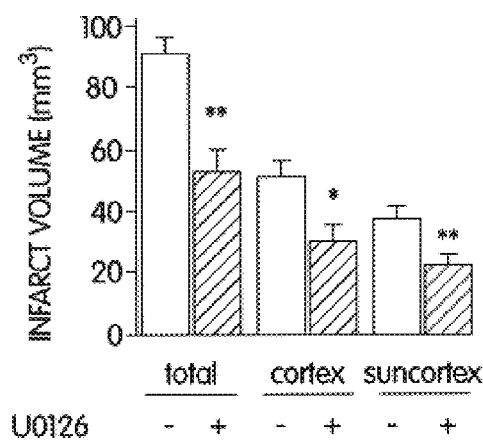
Figure 8C:
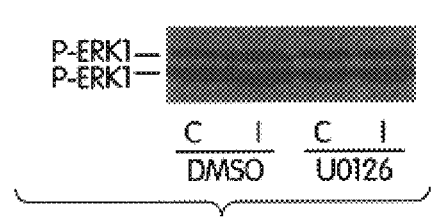
Figure 8D:

Next, it was examined whether delayed injection of U0126 during ischemia protects brain against transient focal cerebral ischemia. Intravenous administration of U0126 (200 µg/kg) 10 minutes before reperfusion following reversible MCAO for 3 hours was significantly protective 24 hours after reperftision (by 40%, P=0.008) when compared to the infarct volume of the vehicle-treated group (FIG. 8B). The degree of phosphorylation of ERK1/2 on immunoblots between DMSO- and U0126-injected mice was compared. The level of phosphorylation, evaluated by the density of phospho-ERK2 immunoblots from the ischemic hemisphere, was significantly less in U0126-treated mice (by 27.4%, p=0.026, n=3) (FIG. 8C). U0126 also reduced phospho-ERK1/2 immunostaining in the damaged brain areas (FIG. 8D).

In this study, it was found that delayed intravenous systemic administration of U0126, a specific MEK1 inhibitor, unexpectedly and significantly reduced the level of brain damage observed following transient focal cerebral ischemia (3 hours). At the dosage used, no altered physiological parameters or abnormal behaviors were observed in connection with the systemic administration of U0126. The present results are consistent with the results of Example 2 demonstrating brain protection against 2 hours focal cerebral ischemia by MEK1 inhibition with PD98059. Moreover, the therapeutic opportunity is significantly extended by using U0126, with respect to the severity of ischemia, the therapeutic temporal window for drug administration, and the route for drug administration. Delayed (1 hour) administration of U0126 was effective in permanent MCAO which is the most severe condition in focal cerebral ischemia (FIG. 8A). In addition, delayed administration, 2 hours 50 minutes after induction of MCAO and 10 minutes before reperfusion, decreased brain infarct by 40% in 3 hours MCAO (FIG. 8B), whereas only pretreatment with intraventricular administration of PD98059, but not injection during ischemia, is protective in 2 hours MCAO.

The extended therapeutic opportunity by U0126, compared with PD98059, may be explained by the following facts: U0126 is more potent than PD98059; while U0126 inhibits active and inactive MEK1, PD98059 has been shown to inhibit the activation of MEK1, but cannot efficiently inhibit MEK1 once it is activated (Favata et al., 1998; DeSilva et al., 1998). In addition, better solubility of U0126 might also contribute to the greater protection observed in vivo. The degree of protection and temporal window is similar to those obtained by using noncompetitive N-methyl-D-aspartate (NMDA) receptor antagonist MK801 (Simon et al., Science 226:850, 1984), the immunosuppressant FK506 (Sharkey et al., Nature 371:336, 1994; Butcher et al., J. Neurosci. 17:6939, 1997) or the caspase inhibitor zVAD-fmk (Hara et al., Proc. Acad Nat'l Sci. USA 94:2007, 1997; Ma et al., Br. J. Pharmacol. 124:756, 1998). The data from in vitro experiments using rat primary cortical neurons subjected to glutamate or hypoxia strongly support the neuroprotective effacy of U0126 against ischemia/reperfusion in vivo, clearly showing the importance of MEK activation in neuronal injury due to ischemia/reperfusion.

Taken together, it is suggested that MEK inhibition with U0126 could contribute to brain protection in vivo against ischemia and reperfusion by not only postsynaptic but also presynaptic mechanisms, thus possibly explaining the profound protection in vivo with U0126 at the extremely low concentrations in the brain estimated by calculation (~1 nM), when compared with the effective concentration in vitro (3–10 µM).

The results from in vivo experiments are quite significant for the therapeutic implications in human stroke, especially in relation to the thrombolysis therapy for cerebral arterial occlusion. The U.S. Food and Drug Administration has approved intravenous injection of tissue plasminogen activator, when applied within 3 hours of the insult, as the first intervention for the treatment of brain ischemia with the hope of dissolving the blood clot that causes brain damage (rt-PA Stroke Study Group, N. Engl. J. Med. 333:1581, 1995); Hacke et al. JAMA 274:1017, 1995). As demonstrated above, ERK2 is dramatically phosphorylated by reperfusion following arterial occlusion, initiating brain damage. Therefore, it is highly likely that MEK1 inhibition can provide additional protective effects to thrombolysis therapy by blocking injury due to reperfusion resulting from arterial recanalization by tissue plasminogen activator.

Example 5

Intravenous Systemic Administration of U0126 Extends Therapeutic Opportunity for the Treatment of Brain Attack Caused by Reperfusion Following Ischemia The experiments below demonstrate that U0126 can protect the brain against reperfusion following blockade of cerebral blood flow in a gerbil model for cardiac arrest and stroke.

Figure 9A:
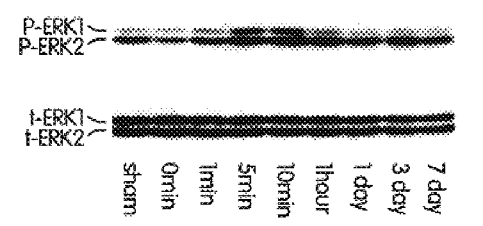
FIG. 9 Reperfusion following forebrain ischemia increases phosphorylation of ERK1/2 in the gerbil hippocampus. (A) Time-dependent changes in phospho-ERK1/2 (upper) and total ERK1/2 (lower) in the hippocampus after 3.5 min bilateral carotid artery occlusion (BCAO). Lysates (30 $\mu$g per lane) from hippocampal tissues were subjected to SDS-PAGE and immunoblotting using phospho-ERK1/2 antibody (New England Biolabs) (upper) or ERK1/2-specific antibodies (Santa Cruz Biotechnology) (lower). ERK1/2 were dramatically dephosphorylated during ischemia (0 min) and rephosphorylated above sham control levels at 5 to 10 min after reperfusion (upper), whereas the levels of total ERK 1/2 protein did not change over time (lower). (B) Immunostaining of sham-control or ischemic brains after 10 min or 1 h of reperfusion using total ERK2 (t-ERK2) or phospho-ERK1/2 (P-ERK 1/2) antibodies. Scale bar: 1 mm. (C) Confocal microscopic images document the localization of phospho-ERK1/2 immunoreactivity and NeuN (CNS neuronal specific marker) immunoreactivity in single tissue section from subfield CA1 after 10 min reperfusion following 3.5 min BCAO. Phospho-ERK1/2 and NeuN were labeled with Alexa Fluor 546 conjugated goat anti-rabbit antibody (red) and Alexa Fluor 488 conjugated streptavidin (green), respectively. Scale bar: 100 $\mu$m.

Reperfusion Following Forebrain Ischemia Increases Phosphorylation of ERK1 and ERK2 (ERK 1/2) in the Hippocampus The gerbil ischemia model was utilized to determine whether ERK1/2 are phosphorylated in the hippocampus after forebrain ischemia and reperfusion. Because gerbils lack the posterior communicating artery that connects carotid artery system and vertebro-basilar artery system, simple bilateral carotid artery occlusion (BCAO) in the gerbil can induce ischemic impact in the forebrain without affecting the vital center in the brain stem. Changes in phosphorylation of ERK1/2 were examined using a phospho-specific ERK1/2 antibody. ERK1/2 were dephosphorylated at the end of 3.5 minutes BCAO. There was a prominent increase in phosphorylation of ERK1/2 in the hippocampus after 5 to 10 minutes of reperfusion following 3.5 minutes of BCAO (FIG. 9A, upper). However, the total ERK1/2 protein levels did not change during reperfusion (FIG. 9A, lower). These results indicated that ERK1/2 are activated by reperfusion.

Figure 9B:
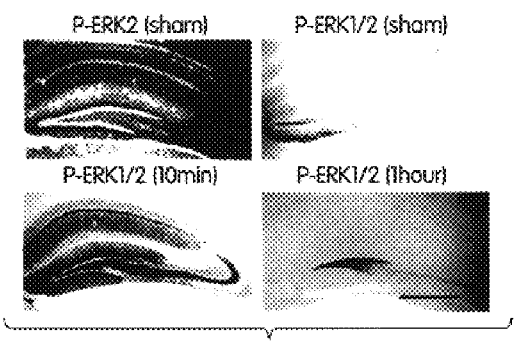
Figure 9C:
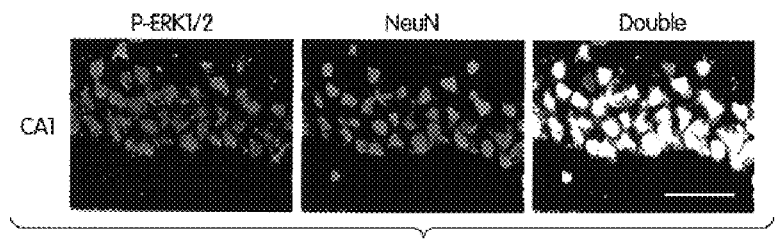

To know in which cell type the phosphorylation of ERK1/2 is increased immunostaining was done using phospho-ERK1/2 antibody on brain sections. Total-ERK1/2 immunostained cells were found throughout the hippocampus, while little phospho-ERK1/2 was detected in the sham-operated animals. After 10 minutes of reperfusion, intense phospho-ERK 1/2 immunostaining was detected in the CA1, dentate gyrus, and mossy fibers, but not in the CA3 pyramidal cells which survive 3.5 minutes BCAO (FIG. 9B). Closer analysis of CA1 pyramidal cells revealed phospho-ERK1/2 immunostaining in both cytoplasm and nucleus (FIG. 9C). Phospho-ERK1/2 immunostaining returned to the basal levels in these areas by 1 hour after reperfusion, with some phospho-ERK1/2 immunostaining remained in the hilar region at one hour (FIG. 9B).

Reperfusion Following Forebrain Ischemia Does Not Increase Phosphorylation of p38 Protein Kinase and JNK in the Hippocampus The possibility of other MAPK subfamilies being activated by reperfusion in the hippocampus was investigated with immunoblotting. No apparent increase in the phosphorylation of p38 protein kinase or JNK was detected in the hippocampus by immunoblotting using phospho-specific p38 protein kinase antibody and phospho-specific JNK antibody, respectively (FIG. 10). These results suggest that MEK/ERK pathway is specifically activated by reperfusion following ischemia in the hippocampus.

Protective Pretreatments Diminish Immunostaining of Phospho-ERK1/2 in the CA1 Pyramidal Cells To address whether phosphorylation of ERK1/2 in the CA1 pyramidal cells is specifically involved in cell death, reperfusion following sublethal ischemia was examined to determine whether it resulted in increased phosphorylation of ERK1/2 in the CA1 pyramidal cells. One minute BCAO, which does not induce neuronal death in the CA1 pyramidal cells, increased phospho-ERK1/2 immunostaining in the dentate granule cells and mossy fibers, similar to what was seen after 3.5 minutes BCAO. Minor staining was observed in the stratum radiatum and stratum oriens of the CA1. However, phospho-ERK1/2 immunostaining was barely detectable in the CA1 pyramidal cell layer after 10 minutes reperfusion (FIG. 11A, compare with FIG. 9B).

The effects of several protective pretreatments were also examined, including ischemic preconditioning by repeated 2 minutes BCAO (see Kitagawa, et al, *Brain Res.* 528: 21–24, 1990); lesioning of the iposlateral entorhinal cortex (see Wielock, et al, *Neurol Res.*:7, 24–26, 1985); and hypothermia (32° C.) (see Buchan and Pulsinelli, *J. Neurosci.* 10: 311–316, 1990) on phospho-ERK1/2 immunostaining in the CA1 pyramidal cells subjected to 3.5 minutes BCAO. These three pretreatments markedly diminished phospho-ERK1/2 immunostaining in the CA1 pyramidal cells after 3.5 minutes BCAO and 10 minutes reperfusion; however, ischemic preconditioning and lesioning of the entorhinal cortex did not appreciably affect phospho ERK1/2 immunostaining in the dentate gyrus and mossy fibers (FIG. 11B). These results suggest that activation of ERK1/2 is specifically involved in the death of the CA1 pyramidal cells caused by ischemia and reperfusion.

Figure 12A:
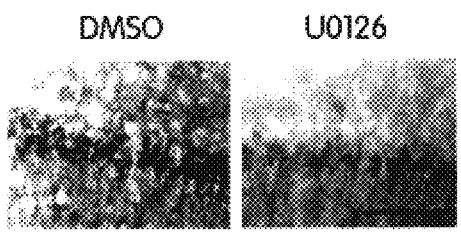
FIG. 12 Effects of intravenous administration of U0126 upon phosphorylation of ERK1/2 (A,B) and neuronal death (C,D) in the CA1 after 3.5 min bilateral carotoid artery occlusion (BCAO). (A) Phospho-ERK1/2 immunostaining of the subfield CA1 from DMSO- or U0126-treated gerbils. Two hundred µl of 0.4% DMSO in 0.1 M PBS with (right) or without (left) U0126 (100 µg/kg b.w.) was administered intravenously 10 min before 3.5 min BCAO, and the brains were examined after 10 min of reperfusion. Scale bar: 200 µm. (B) The number of phospho-ERK1/2 immunoreactive CA1 pyramidal cells. Two hundred µl of 0.4% DMSO in 0.1 M PBS containing U0126 (0, 50 or 100 µg/kg b.w.) was injected intravenously 10 min before ischemia. Statistical analysis was done by ANOVA followed by Bonferroni. Double asterisks, P<0.01; triple asterisks, P<0.001 compared with the DMSO-injected group. Data are presented as mean +SEM (n=6–8). (C) Photomicrographs of the subfield CA1 from DMSO- and U0126-administrated gerbils. DMSO or U0126 was administrated gerbils. DMSO or U0126 was administrated intravenously 10 min before 3.5 min BCAO, and the brains were evaluated 7 d after reperfusion. Brain sections were stained with 0.1% cresyl violet. Scale bar: 200 µm. (D) The number of viable CA1 pyramidal cells. Two hundred µl of 0.1 M PBS containing U0126 (0, 50 or 100 µtg/kg b.w.) was injected intravenously 10 min before ischemia, and the gerbils were allowed to survive for 7 d after reperfusion. The number of viable CA1 pyramidal cells was expressed as the cell number per 1 mm length of subfield CA1. Triple asterisks, P<0.001 compared with the DMSO-injected group (ANOVA followed by Bonferroni). Data are presented as mean±SEM (n=5–8).
Figure 12B:
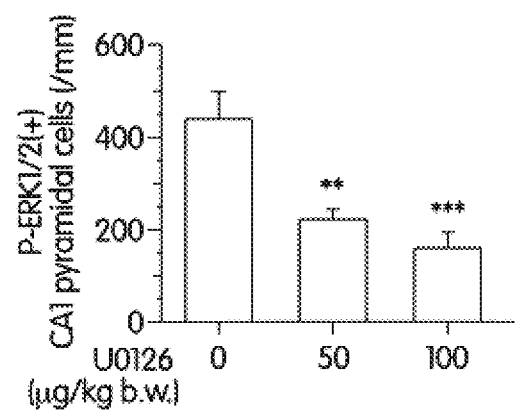
Figure 12C:
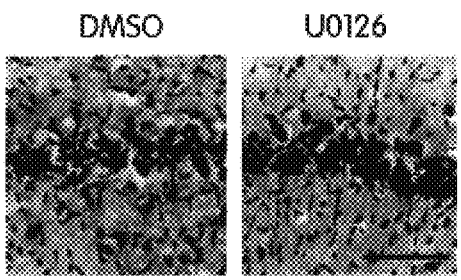
Figure 12D:
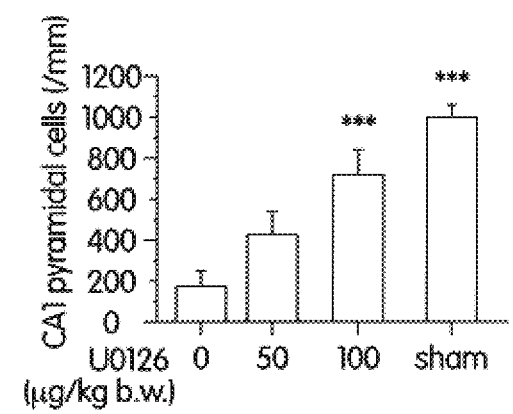

Intravenous Administration of U0126 Attenuates Hippocampal Injury Caused by Reperfusion Following Forebrain Ischemia in Gerbils To examine whether inhibition of MEK1/2, which are activators of ERK1/2, protects the CA1 pyramidal cells, U0126 was intravenously administered in gerbils subjected to 3.5 minutes BCAO. The study confirmed that intravenous administration of U0126 (50 or 100 μg/kg b.w. in 200 μl of 0.4% DMSO in 0.1M PBS) 10 minutes before ischemia reduced the number of phospho-1/2 immunoreactive CA1 pyramidal cells 10 minutes after reperfusion in a dose-dependent manner (FIG. 12A, B). Intravenous administration of U0126 10 minutes before ischemia decreased the loss of CA1 pyramidal cells at 7 days (FIG. 12C, D). Intravenous systemic administration of U0126 at these dosages did not affect the core temperature during ischemia and up to 6 hours after reperfusion (Table 4). Thus, MEK1/2 inhibition with intravenous administration of U0126 protects CA1 pyramidal cells against reperfusion following forebrain ischemia, strongly implicating ERK1/2 activation in the death of CA1 pyramidal cells following ischemia and reperfusion.

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference.

What is claimed is:

1. A pharmaceutical composition comprising
   a MEK1 inhibitor, and
   a non-MEK1 inhibitor anti-stroke agent selected from the group consisting of N-methyl-D-aspartate (NMDA) receptor antagonists, immunosuppressants and caspase inhibitors, together in an amount effective for treating an ischemic condition.

2. The method of claim 1, wherein the non-MEK1 inhibitor anti-stroke agent is selected from the group consisting of MK801, FK506 and zVAD-fmk.

3. A method for treating a subject having a condition characterized by ischemia comprising
   administering to a subject in need of such treatment a MEK1 inhibitor in an amount effective to reduce MEK1 activity, wherein the subject is free of symptoms otherwise calling for treatment with the MEK1 inhibitor, and wherein the MEK1 inhibitor is a (phenylthio)butadiene compound.

4. The method of claim 1, wherein the symptoms otherwise calling for treatment with the MEK1 inhibitor are the symptoms of a proliferative disease.

5. The method of claim 3, wherein the MEK1 inhibitor is selected from the group consisting of 1,4-diamino-2,3-dicyano-1,4-bis-(phenylthio)butadiene (U0125) and 1,4-diamino-2,3-dicyano-1,4-bis-(2-aminophenylthio)butadiene (U0126).

6. The method of claims 3, 4 or 5, wherein the MEK1 inhibitor is administered to a subject who has had an ischemic stroke.

7. The method of claims 3, 4 or 5, wherein the MEK1 inhibitor is administered prophylactically to a subject at risk of having an ischemic stroke.

8. The method of claims 3, 4 or 5, wherein the MEK1 inhibitor is administered parenterally to a subject.

9. A method for treating a subject having a condition characterized by hypoxia comprising
   administering to a subject in need of such treatment a MEK1 inhibitor in an amount effective to reduce MEK1 activity, wherein the subject is free of symptoms otherwise calling for treatment with the MEK1 inhibitor.

10. The method of claim 9, wherein the MEK1 inhibitor is a (phenylthio)butadiene compound.

11. The method of claim 10, wherein the MEK1 inhibitor is selected from the group consisting of 1,4-diamino-2,3-dicyano-1,4-bis-(phenylthio)butadiene (U0125) and 1,4-diamino-2,3-dicyano-1,4-bis-(2-aminophenylthio)butadiene (U0126).

12. A method for treating a subject having a condition characterized by glutamate toxicity comprising
   administering to a subject in need of such treatment a MEK1 inhibitor in an amount effective to reduce MEK1 activity, wherein the subject is free of symptoms otherwise calling for treatment with the MEK1 inhibitor.

13. The method of claim 12, wherein the MEK1 inhibitor is a (phenylthio)butadiene compound.

14. The method of claim 13, wherein the MEK1 inhibitor is selected from the group consisting of 1,4-diamino-2,3-dicyano-1,4-bis-(phenylthio)butadiene (U0125) and 1,4-diamino-2,3-dicyano-1,4-bis-(2-aminophenylthio)butadiene (U0126).

* * * * *

UNITED STATES PATENT AND TRADEMARK OFFICE
CERTIFICATE OF CORRECTION

PATENT NO. : 6,319,955 B1
DATED : November 20, 2001
INVENTOR(S) : Alessandrini et al.

It is certified that error appears in the above-identified patent and that said Letters Patent is hereby corrected as shown below:

<u>Column 30, claim 2,</u>
Line 9, please delete "method" and insert -- composition -- therefor.

Signed and Sealed this

Fifth Day of March, 2002

Attest:

*Attesting Officer*

JAMES E. ROGAN
*Director of the United States Patent and Trademark Office*